United States Patent [19]
Wodlinger et al.

[11] Patent Number: 5,743,859
[45] Date of Patent: Apr. 28, 1998

[54] INTEGRATED ELECTRICAL SIGNAL SWITCHING AND AMPLIFYING SYSTEM

[75] Inventors: Harold Max Wodlinger, Thornhill; Richard Michael Fine, Mississauga, both of Canada

[73] Assignee: Quinton Electrophysiology Corporation, Richmond Hill, Canada

[21] Appl. No.: 648,529

[22] Filed: May 13, 1996

Related U.S. Application Data

[63] Continuation of Ser. No. 219,692, Mar. 29, 1994, Pat. No. 5,566,096, which is a continuation-in-part of Ser. No. 975,768, Nov. 13, 1992, abandoned.

[51] Int. Cl.[6] .................................................. A61B 5/04
[52] U.S. Cl. ................................ 600/522; 600/509
[58] Field of Search .......................... 128/709, 710, 128/696; 607/9, 18, 23; 600/522, 523, 509, 374

[56] References Cited

U.S. PATENT DOCUMENTS

| | | | |
|---|---|---|---|
| 3,960,141 | 6/1976 | Bolduc | 128/2.06 E |
| 4,037,586 | 7/1977 | Grichnik | 128/2.1 B |
| 4,201,224 | 5/1980 | John | 128/731 |
| 4,249,538 | 2/1981 | Musha et al. | 128/630 |
| 4,367,753 | 1/1983 | Jirak | 128/708 |
| 4,380,237 | 4/1983 | Newbower | 128/693 |
| 4,416,288 | 11/1983 | Freeman | 128/731 |
| 4,417,306 | 11/1983 | Citron et al. | 364/415 |
| 4,513,752 | 4/1985 | Weyant | 128/696 |
| 4,522,212 | 6/1985 | Gelinas et al. | 128/642 |
| 4,550,370 | 10/1985 | Baker | 364/413 |
| 4,624,263 | 11/1986 | Slavin | 128/710 |
| 4,628,937 | 12/1986 | Hess et al. | 128/642 |
| 4,641,649 | 2/1987 | Walinsky et al. | 128/303.1 |
| 4,674,518 | 6/1987 | Salo | 128/695 |
| 4,677,986 | 7/1987 | Decote, Jr. | 128/697 |

(List continued on next page.)

FOREIGN PATENT DOCUMENTS

WO 95/20347 8/1995 WIPO.

OTHER PUBLICATIONS

Bloom Associates, Ltd.; "Model BPA Cardiovascular Pressure Amplifier" Data Sheet BA.DAT3; date unknown; one page.

Gould Electronics; "Gould: Where Innovation Is a Practical Art" Bulletin 426-3; Apr. 1991; eight pages.

Bloom Associates, Ltd.; "Total Cardiac Electrophysiology System—Total Commitment to Service"; date unknown; six pages.

Arrhythmia Research Technology, Inc.; "CARDIOLAB Specifications"; date unknown; three pages.

Bloom Associates, Ltd.; "BERS-400A EP Recording Amplifiers and Input Switching System" Data Sheet BA.DAT2; date unknown; 3 pages.

*Primary Examiner*—William E. Kamm
*Assistant Examiner*—Kennedy J. Schaetzle
*Attorney, Agent, or Firm*—Richard D. Allison

[57] ABSTRACT

A signal management system is disclosed which integrates a patient switching box and an amplification unit into a single compact enclosure sufficiently small to reside by the patient table in an operating unit set up for electrophysiology procedures. The system includes a front panel designed to accept standard ECG leads, a plurality of intracardiac leads, including leads available for stimulation and/or lesion generation, and a plurality of pressure channels. The front panel also includes a touch screen display to allow quick assignments of labels to each of the ECG or intracardiac leads and the pressure channels. The system includes an onboard microprocessor which allows any operation performed on the System to be automatically updated on a remote computer processing unit if attached, and vice-versa. Digital signal processors are used in the system to perform switching operations on the electrical signals received, and to perform gain, limiting and/or filtering processes thereon. The digital signal processors are automatically calibrated to adjust for varying gain and phase performance of the inputting front-end amplifiers which deliver the electrical signals from the intracardiac leads.

30 Claims, 20 Drawing Sheets

U.S. PATENT DOCUMENTS

| | | | |
|---|---|---|---|
| 4,682,596 | 7/1987 | Bales et al. | 128/303.14 |
| 4,686,988 | 8/1987 | Sholder | 128/419 PT |
| 4,695,955 | 9/1987 | Faisandier | 364/413 |
| 4,699,147 | 10/1987 | Chilson et al. | 128/642 |
| 4,705,043 | 11/1987 | Imran | 128/419 PG |
| 4,836,214 | 6/1989 | Sramek | 128/693 |
| 4,852,580 | 8/1989 | Wood | 128/693 |
| 4,911,174 | 3/1990 | Pederson et al. | 128/695 |
| 4,979,510 | 12/1990 | Franz et al. | 128/642 |
| 5,016,631 | 5/1991 | Hogrefe | 128/419 PS |
| 5,018,523 | 5/1991 | Bach et al. | 128/419 PG |
| 5,041,973 | 8/1991 | Lebron et al. | 364/413.05 |
| 5,058,583 | 10/1991 | Geddes et al. | 128/419 D |
| 5,058,599 | 10/1991 | Andersen | 128/705 |
| 5,086,778 | 2/1992 | Mueller et al. | 128/696 |
| 5,092,339 | 3/1992 | Geddes et al. | 128/692 |
| 5,101,832 | 4/1992 | Pritchard et al. | 128/696 |
| 5,109,870 | 5/1992 | Silny et al. | 128/780 |
| 5,137,019 | 8/1992 | Pederson et al. | 128/419 PG |
| 5,156,151 | 10/1992 | Imran | 128/642 |
| 5,195,968 | 3/1993 | Lundquist et al. | 604/95 |
| 5,197,467 | 3/1993 | Steinhaus et al. | 128/419 PG |
| 5,224,475 | 7/1993 | Berg et al. | 128/419 D |
| 5,228,442 | 7/1993 | Imran | 128/642 |
| 5,233,515 | 8/1993 | Cosman | 364/413.02 |
| 5,239,999 | 8/1993 | Imran | 128/642 |
| 5,246,008 | 9/1993 | Mueller | 128/695 |
| 5,255,679 | 10/1993 | Imran | 128/642 |
| 5,279,299 | 1/1994 | Imran | 128/642 |
| 5,282,840 | 2/1994 | Hudrlik | 607/28 |
| 5,293,869 | 3/1994 | Edwards et al. | 128/642 |
| 5,297,549 | 3/1994 | Beatty et al. | 128/642 |
| 5,309,910 | 5/1994 | Edwards et al. | 128/642 |
| 5,313,943 | 5/1994 | Houser et al. | 128/642 |
| 5,324,284 | 6/1994 | Imran | 606/15 |
| 5,334,193 | 8/1994 | Nardella | 606/41 |
| 5,341,807 | 8/1994 | Nardella | 128/642 |
| 5,345,936 | 9/1994 | Pomeranz et al. | 128/642 |
| 5,357,956 | 10/1994 | Nardella | 128/642 |
| 5,365,926 | 11/1994 | Kyu | 128/710 |
| 5,383,874 | 1/1995 | Jackson et al. | 606/1 |
| 5,383,917 | 1/1995 | Desai et al. | 607/702 |
| 5,397,339 | 3/1995 | Desai | 607/116 |
| 5,406,946 | 4/1995 | Imran | 128/642 |
| 5,409,000 | 4/1995 | Imran | 128/642 |
| 5,447,529 | 9/1995 | Marchlinski et al. | 607/99 |

| CHANNELS | POLES | GAIN | FILTER | LIMITER | NAME |
|---|---|---|---|---|---|
| ← | | | | | |
| 1 | | | | | |
| 2 | | | | | |
| 3 | | | | | |
| 4 | | | | | |
| 5 | | | | | |
| 6 | | | | | |
| 7 | | | | | |
| 8 | | | | | |
| 9 | | | | | |
| 10 | | | | | |
| 11 | | | | | |
| 12 → | | | | | |
| Main | | | | | |

FIGURE 5(a)

| CHANNELS | POLES | GAIN | FILTER | LIMITER | NAME |
|---|---|---|---|---|---|
| 1 | I | 1000 | Off | Off | I |
| 2 | aVf | 1000 | Off | Off | aVf |
| 3 | V6 | 1000 | Off | Off | V6 |
| 4 | HRA1-WCT | 250 | Off | Off | HRA1-WCT |
| 5 | | | 100 | | |
| 6 | | | 250 | | |
| 7 | | | 500 | | |
| 8 | | | 1000 | | |
| 9 | | | 2500 | | |
| 10 | CS 3-4 | 500 | 5000 | Off | CS 3-4 |
| 11 | | | Done | | |
| 12 | | | | | |

Main

| CHANNELS | POLES | GAIN | FILTER | LIMITER | NAME |
|---|---|---|---|---|---|
| 1 ← | | | | | |
| 2 | 1 Q | 2 W | 3 E | 4 R | 5 T | 6 Y | 7 U | 8 I | 9 O | 0 P | aVf |
| 3 | A | S | D | F | G | H | J | K | L | V6 |
| 4 | | | | | | | | | | |
| 5 | Z | X | C | V | B | N | M | , | . | + | HRA1-WCT ↓ |
| 6 | | | | | Done | | | | | | |
| 7 | | | | | | |
| 8 | | | | | | |
| 9 | | | | | | |
| 10 | CS 3-4 | | 500 | 30-400 Off | Off | |
| 11 | | | | | | |
| 12 → | | | | | CS 3-4 |
| Main | | | | | |

| CHANNELS | POLES | GAIN | FILTER | LIMITER | NAME |
|---|---|---|---|---|---|
| 1 | I | 1000 | 0.05-100 Off | 1.5 | I |
| 2 | aVf | 1000 | 0.05-100 Off | 3.1 | aVf |
| 3 | V6 | 1000 | 0.05-100 Off | Off | V6 |
| 4 | HRA1-WCT | 250 | 0.05-400 Off | Off | HRA1-WCT |
| 5 | CS 3-4 | 500 | 30-400 Off | Off | CS 3-4 |
| 6 | CS 1-2 | 500 | 30-400 Off | Off | CS 1-2 |
| 7 | CS 1-4 | 500 | 30-400 Off | Off | CS 1-4 |
| 8 | VOLTS | 100 | DC-100 Off | Off | VOLTS |
| 9 | CURRNT | 100 | DC-100 Off | Off | CURRNT |
| 10 | AORTA | 300 | DC-40 Off | Off | AORTA |
| 11 | | | | | |
| 12 | | | | | |

*FIGURE 5(g)*

INTEGRATED ELECTRICAL SIGNAL SWITCHING AND AMPLIFYING SYSTEM

This application is a continuation of U.S. patent application Ser. No. 08/219,692 filed on Mar. 29, 1994, now U.S. Pat. No. 5,556,096, which is a continuation-in-part of U.S. patent application Ser. No. 975,768 filed Nov. 13, 1992, now abandoned.

BACKGROUND OF THE INVENTION

1. Field of the Invention

This invention relates generally to an electrical signal management system. More specifically, the present invention relates to an integrated system for electrical signal switching and amplifying. Also, the present invention relates to an automatic calibration system for calibrating the electrical signal switching and amplifying hardware in the integrated system.

2. Prior Art

Electrophysiology signal amplification systems commonly include a switch box generally located at a patient's bedside during an electrophysiology procedure. The switch box receives the proximal ends of intracardiac catheter leads, ECG leads, blood pressure sensor leads, breathing sensor leads, temperature sensor leads, pulse sensor leads, or the like. The leads are input by attaching them to input terminals which are arranged on the switch box in a grid-type fashion and labelled for identification either numerically or by color. The switch box outputs to an amplifier which in turn outputs to a computer processing unit, which also in turn may output to a monitor or chart recorder if desired.

During setup of the switch box, the computer processing unit must receive information identifying the input locations of each of the leads in the input terminal grid. This is commonly accomplished by having one operator at the patient's bedside attach the leads in one-by-one fashion into the switch box, and then announce to a second operator the identification of each input terminal label corresponding to the particular lead being inserted. The second operator then simultaneously inputs into the computer processing unit the label indicating the particular parameter being monitored and the corresponding output terminal identification number or color as it announced by the first operator.

After the leads have been attached to the switch box and the computer processing unit has received the necessary labels related to the positioning of the leads and the related input terminal numbers or colors to which the leads correspond, the procedure is commenced. However, very often during an electrophysiology procedure, it is desirable to either move a catheter to a different position in the patient's heart, to add a catheter, or to compare signals received from various catheters. In any of these events, it is necessary to re-identify the particular label given to the catheter lead so that the changes or additions may be properly input into the computer processing unit. Because of the physical separation of the switch box and the computer processing unit, and the necessity of having two operators perform redundant operations to ensure that the computer processing unit correctly correlates the label of the catheter lead with its position in the switch box, necessary changes during a procedure can cause errors in the analysis data to occur, as well as potential injury to the patient.

Attempts have been made to solve the problem of input terminal/lead label correspondence during setup and operational use of signal acquisition and processing systems such as the electrical signal management system of the present invention, with varying success. For example, U.S. Pat. No. 4,037,586 to Grichnick, describes an electroencephalograph which includes a visual display panel which is actuated in response to digital signals for indicating the particular pattern in which electrodes connected to the patient are processed to provided desired output signals. Although this invention may help an operator view the particular processing order of signals received by the device, it nevertheless fails to assist the physician in setup of the device for operation or in changing the setup during a procedure.

U.S. Pat. No. 4,695,955 issued to Faisandier, describes a prior art electronic device which acquires and processes signals originating from sensors attached to a patient. The device automatically recognizes a sensor lead attached to an input terminal thereof due to the mechanical design of the lead itself, and automatically programs the processing system thereof for the proper signal amplification, energization, and processing elements. This device simplifies setup of a procedure by automatically recognizing the particular lead attached to the input terminal. It nevertheless contains the drawback of requiring the use of leads which can be mechanically identified by the device to initiate automatic programming of the processing system. Further, the device fails to allow relabelling of a lead depending on a change in the corresponding sensors position on the patient, and/or a change in the particular parameter being monitored by the sensor.

OBJECTS AND SUMMARY OF THE INVENTION

An object of the present invention is to provide an electrical signal management system which considerably simplifies preprocedure calibration and setup, and also simplifies setup changes during an ongoing signal acquisition and processing procedure.

Another object of the present invention is to provide an integrated system for electrical signal switching and amplifying which is sufficiently small to be mounted at a patient's bedside.

A further object of the present invention is to provide an integrated electrical signal switching and amplifying system which can be completely and independently setup and controlled by an operator at the patient's bedside without the necessity of a second operator recording input terminal identification numbers or colors to an attached computer processing unit as a manner of identifying the output terminal positions of sensor leads.

It is a further object of the present invention to provide an integrated electrical signal switching and amplification system which can function totally independently of any data processing device which may be attached thereto.

It is also an object of the present invention to provide an integrated electrical signal switching and amplifying system which provides analog output therefrom for allowing attachment of an analog monitor, chart recorder, and/or computer processing unit, such that monitoring and/or recording of signals output from the integrated electrical signal switching and amplifying system can be accomplished by a prior art analog monitor and/or chart recorder even in the absence of a computer processing unit or during periods of malfunction or breakdown of the computer processing unit.

It is another object of the present invention to provide an interactive display screen and software for simplifying setup and operation of the integrated electrical signal switching and amplifying system.

It is also an object of the present invention to provide the integrated electrical signal switching and amplifying system having an onboard microprocessing capability which allows total functioning thereof independently from any outside computer processing unit and allows storage of predetermined setup configurations for simplification of the setup procedure.

It is further an object of the present invention to provide the integrated electrical signal switching and amplifying system with an electrical hardware design which significantly reduces the overall size of the system to allow it to be mounted at a patient's bedside to facilitate an operator's use thereof during an electrophysiology procedure.

It is a further object of the present invention to provide an automatic calibration system for calibrating.

These and other objects of the present invention are realized in a presently preferred embodiment thereof, disclosed by way of example and not by way of limitation, which includes an integrated electrical signal switching and amplifying system for use in electrophysiology procedures as an interface between electrical signals received from a patient through sensors such as intracardiac catheters, ECG leads, pressure sensors or the like, and an analog monitor, chart recorder, or computer processing unit. The system uses digital technology to amplify and condition electrical signals from a patient's heart and download analog formatted signals to a computer processing unit or a traditional analog monitor or chart recorder.

The analog output of the system of the present invention has a unique safety advantage over prior art electrophysiology amplification systems in that it ensures the possibility of uninterrupted electrophysiology studies in the event that a computer processing unit fails during the electrophysiology procedure. For example, a chart recorder could be used alone wish the present invention, or in conjunction with a computer processing unit, to record the electrophysiology procedure. This feature allows the system of the present invention to be used to present information from an electrophysiology procedure entirely independently of a computer processing unit if desired.

The system of the present invention includes a front panel having an interactive display which eliminates potentially confusing cross connections and allows simplified selection and assignment of intracardiac catheters and other sensors during the setup procedure. The system of the present invention also allows catheters or other sensors to be assigned at the patient's bedside by a single operator, and automatically transfers the necessary information to a computer processing unit should it be attached. This eliminates the formerly necessary exchange of information between an attending physician operator at the patient's bedside and a medical technologist operator positioned at the computer processing unit.

The system of the present invention also includes a novel electrical hardware design which improves signal conditioning performance and reduces the systems overall physical size. Specifically, the present invention includes at least one digital signal processors (DSP) for comparing signals received from the input terminals thereof, in lieu of prior art systems which include much more bulky analog switching arrays to accomplish this task.

Further, the present invention includes an automatic calibration system which allows the DSP to perform an automated calibration for correction of any variances in performance of the amplifier components and to ensure proper DSP output.

The system of the present invention can also be adapted for use in hemodynamic studies in conjunction with electrophysiology studies due to its ability to receive and process pressure inputs.

BRIEF DESCRIPTION OF THE DRAWINGS

Other features and advantages of the present invention will become more apparent with reference to the following description of the preferred embodiment and the accompanying drawings in which similar elements are represented by like numerals throughout, and in which:

FIGS. 4(a)–4(g), 5(a)–5(g) and 6(a)–(c) show the display of the preferred embodiment of the integrated electrical signal switching and amplifying system as configured in various modes of setup and operation.

DETAILED DESCRIPTION OF THE PREFERRED EMBODIMENT

Figures 1, 2:
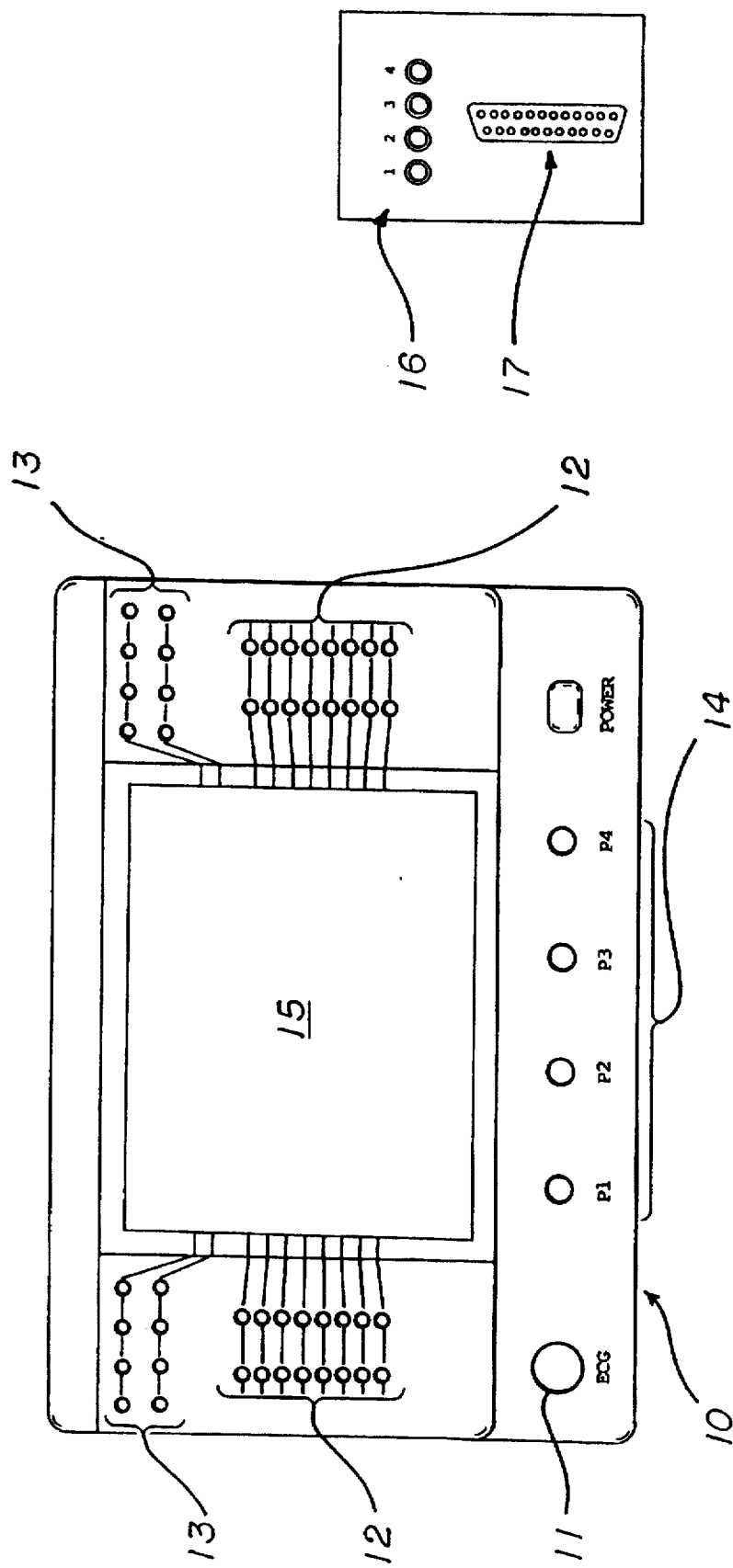
FIG. 1 is a front view of a preferred embodiment of an integrated electrical signal switching and amplifying system formed in accordance with the principles of the present invention showing the front panel thereof.
FIG. 2 is a partial view of the back panel of the preferred embodiment of the integrated electrical signal switching and amplifying system.
Figure 3:
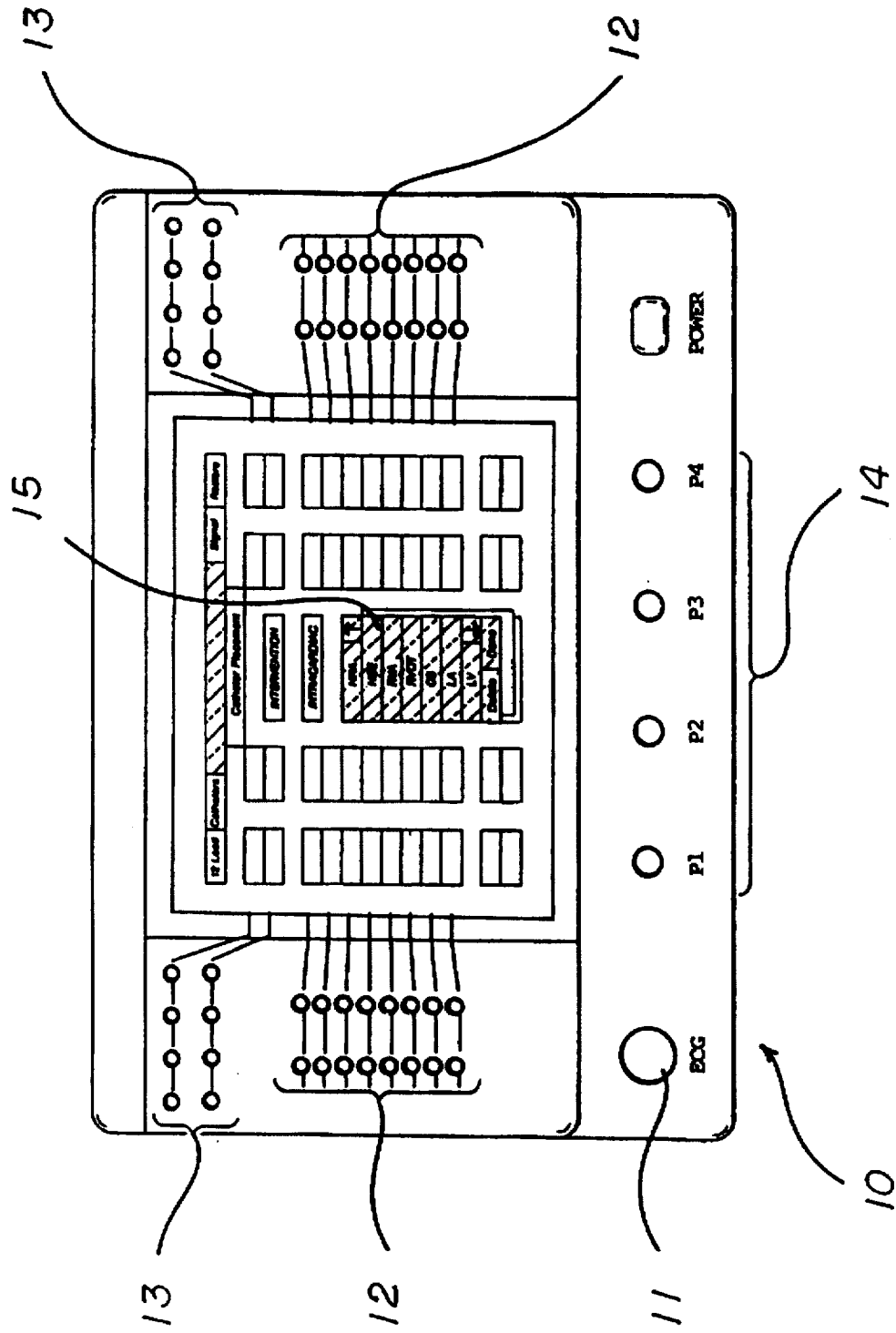
FIG. 3 shows the front panel of the preferred embodiment of the integrated electrical signal switching and amplifying system including the display thereof showing fields positioned thereon for containing labels corresponding to the referenced input terminals.

As shown in the exemplary drawings for the purposes of illustration, an embodiment of an integrated system made in accordance With the principals of the present invention, referred to generally by the reference numeral 10, is provided for simplified setup and operation of an electrophysiology amplifying and switching system during an electrophysiology procedure.

More specifically, as shown in FIG. 1, the front panel of the system 10 of the present invention includes a standard twelve lead ECG input terminal 11 which allows attachment of any well known ECG lead cable through which leads extend from electrodes attached to the chest of a patient in a well known manner for transferring ECG signals into the system 10.

Similarly, intracardiac input terminals 12 are positioned on the front panel, and include intervention/input terminals 13 which can be used as intracardiac input terminals or intervention (stimulation) terminals. The intervention/input terminals 13 are hard wired to corresponding intervention/output terminals 17 (as shown in FIG. 2). The intracardiac input terminals 12 are adapted to receive leads from the intracardiac catheters which have been placed within the patient's heart to sense the electrical signals passing therethrough. The intervention/input terminals 13 are designed to pass electrical stimulation signals (originating from an electrical stimulator, not shown) through the system 10 into the intracardiac catheters. The intervention/input terminals 13 are also designed to receive electrical signals (originating in the heart) from the intracardiac catheters in the same manner as the input terminals 12.

Also included on the front panel are four pressure channel input terminals 14 which are designed for receipt of pressure sensor leads which have been attached to pressure sensors positioned at desired points on or within the patient's body from which blood pressure information is desired.

The dominant feature of the front panel of the system 10 is an operator interactive "touch" display 15 which is programmed by an onboard microprocessor 27 (see FIG. 6) to operate as a labelling area for the input terminals 11, 12, 13, 14, and the auxiliary input terminals 16 (see FIG. 2). The display 15 is also configured by the microprocessor 27 to define touch areas thereon as "soft keys" for use in initiating setup and operation commands as will be explainedbelow, and also to display messages related to setup and operation Of the system 10. Further, the display 15 is driven by a microprocessor 27 (See FIG. 7) to display assignments of the output channels 17 (see FIG. 2) and the labels, poles, gains, filter, and clamp settings through which each channel of entering data must pass when entered into the system 10.

The display 15 is designed to simplify setup and operation of the system 10 as will be explained momentarily. Software preprogrammed into the onboard microprocessor 27, such as by a ROM, is directly responsible for the operation of the display 15 and input "soft keys" thereof. The display 15 is preferably a single 640×480 pixel pressure responsive display commonly referred to as a "touch screen".

Although the present invention is not limited to the following, it is intended that the preferred embodiment of the present invention include the ability to receive twelve leads of ECG signals as input into the input terminal 11. Further, it is preferred that sixteen or thirty-two intracardiac input terminals 12 and eight intervention or intracardiac input terminals 13 be included in the system 10. Further, it is preferred that four pressure channel input terminals 14 be included with four auxiliary input channels 16 (See FIG. 2).

SETUP

Input Channel Selection

The display 15 is used to specify and setup labels associated with each input terminal 12, 13, 14, and 16. To describe the labeling process it is first necessary to define some terms. A label 28 (See FIG. 4(b)) is the alphanumeric assigned to an input terminal to identify the catheter or sensor and the lead attached thereto. A Catheter Group, or simply "group" is a group of labels 28 that have the same prefix letters but different numbers. An example of a Catheter Group would be: "RVA1, RVA2, RVA3, RVA4" (See FIG. 4(c)), where the prefix letters "RVA", are common to each label 28. Any Intracardiac or Intervention labels 28 with the same base letters, regardless of their location on the display 15, belong to the same group. A field 29 (See FIG. 4(a)) is a label location on the display 15.

Figure 4A:
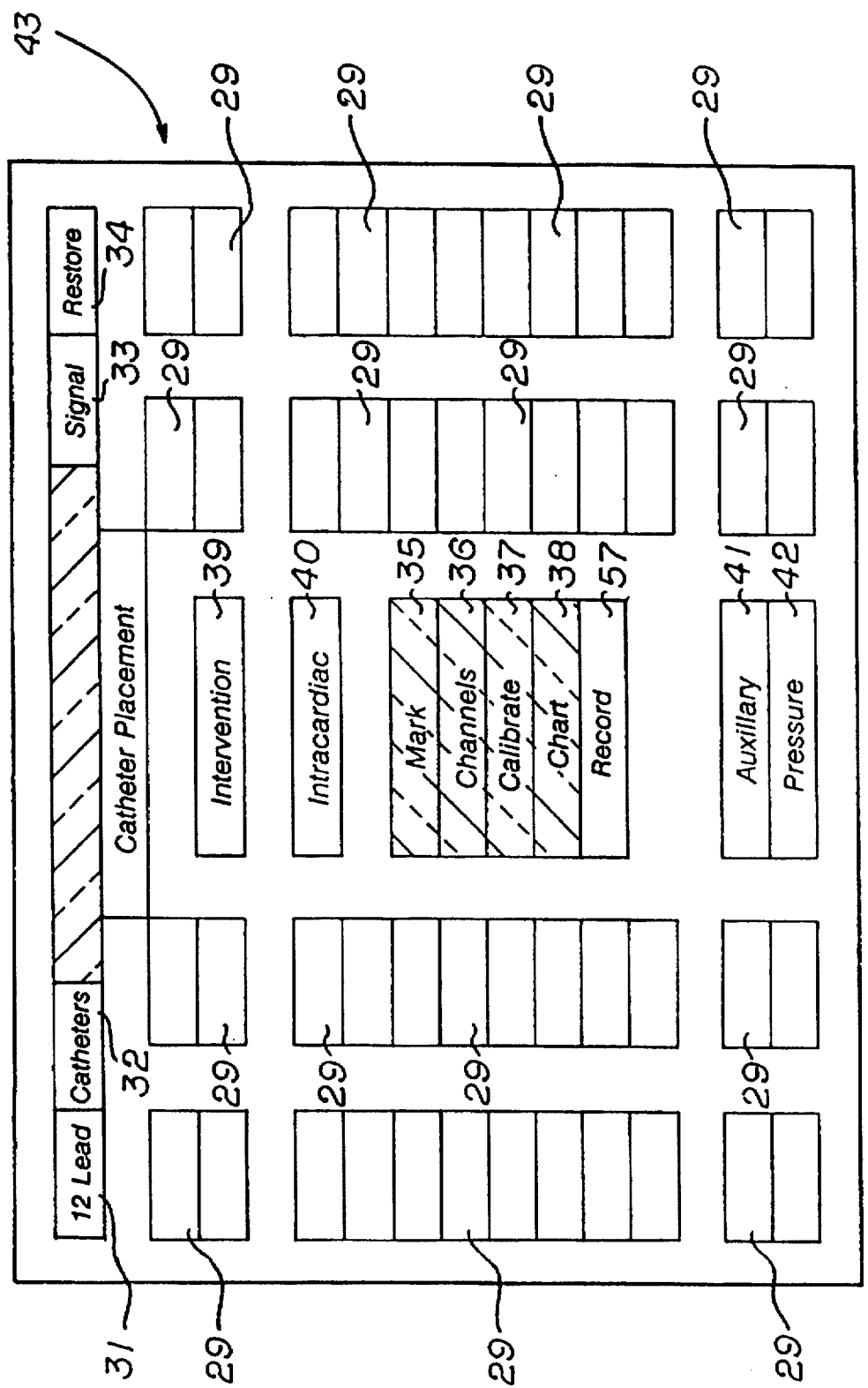
Figure 5A:
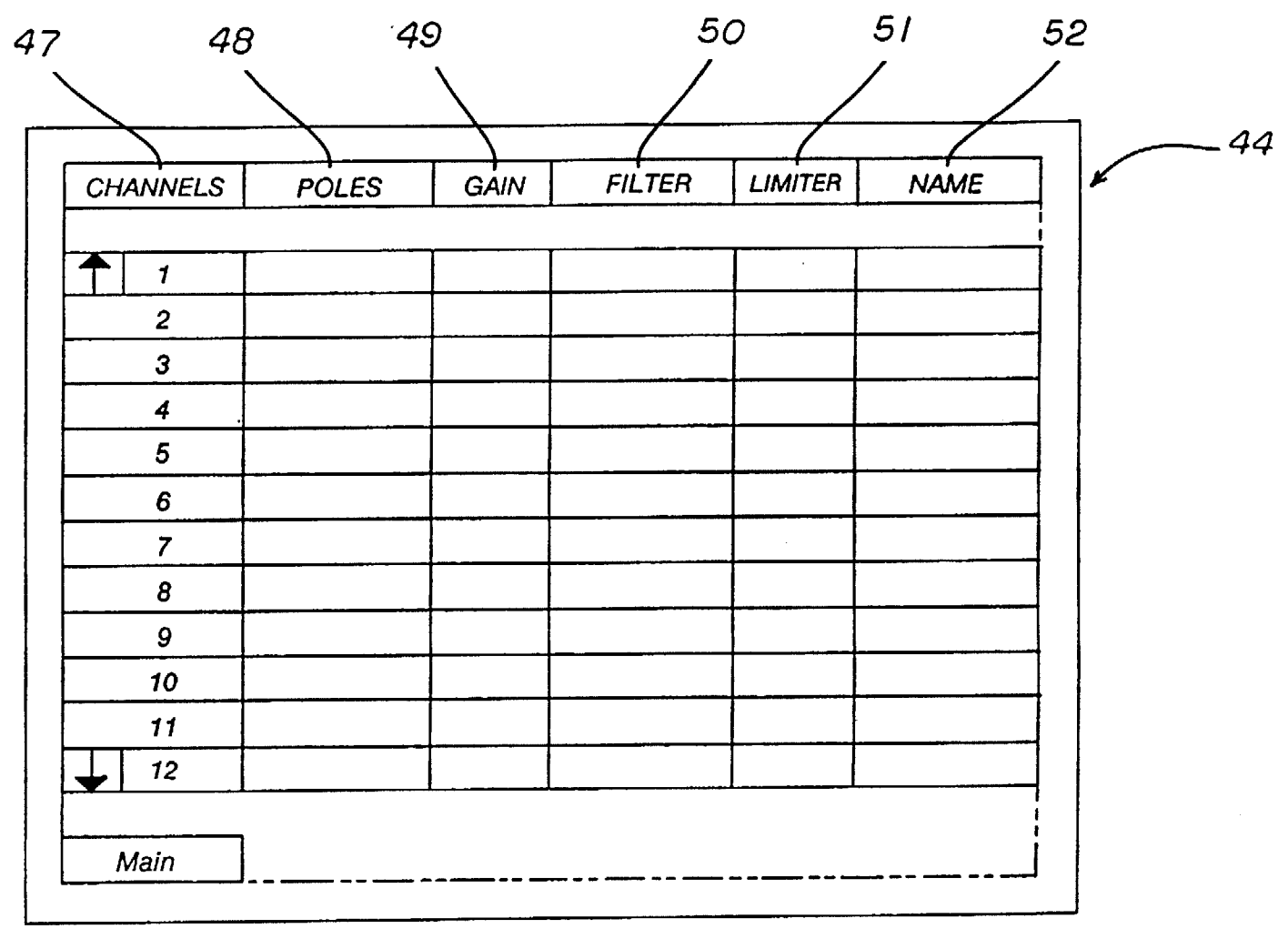

There are two basic screens which can be called to the display 15 by the operator to assist in arranging the setup configuration of the system 10. The first is the "Catheter Placement Screen" 43 as shown in FIG. 4(a). The second is the "Signals Screen" as shown in FIG. 5(a). Once the electrophysiology catheters have been placed in the patient, setup of the system 10 only requires the steps of: 1) Specifying the signal inputs by producing a label 28 for each one, and then 2) Specifying the desired signal output parameters. The first step is accomplished through the use of the Catheter Placement Screen 43, the second step is accomplished with the assistance of the Signals Screen 44.

Referring to FIG. 4(a), the Catheter Placement Screen 43 is programmed to preferably form the following soft keys: a twelve lead key 31, a restore key 34, a catheter key 32, a signals key 33, a mark key 35, a channels key 36, a calibrate key 37, a chart key 38, an intervention key 39, an intracardiac key 40, an auxiliary key 41, and a pressure key 42.

Figure 4B:
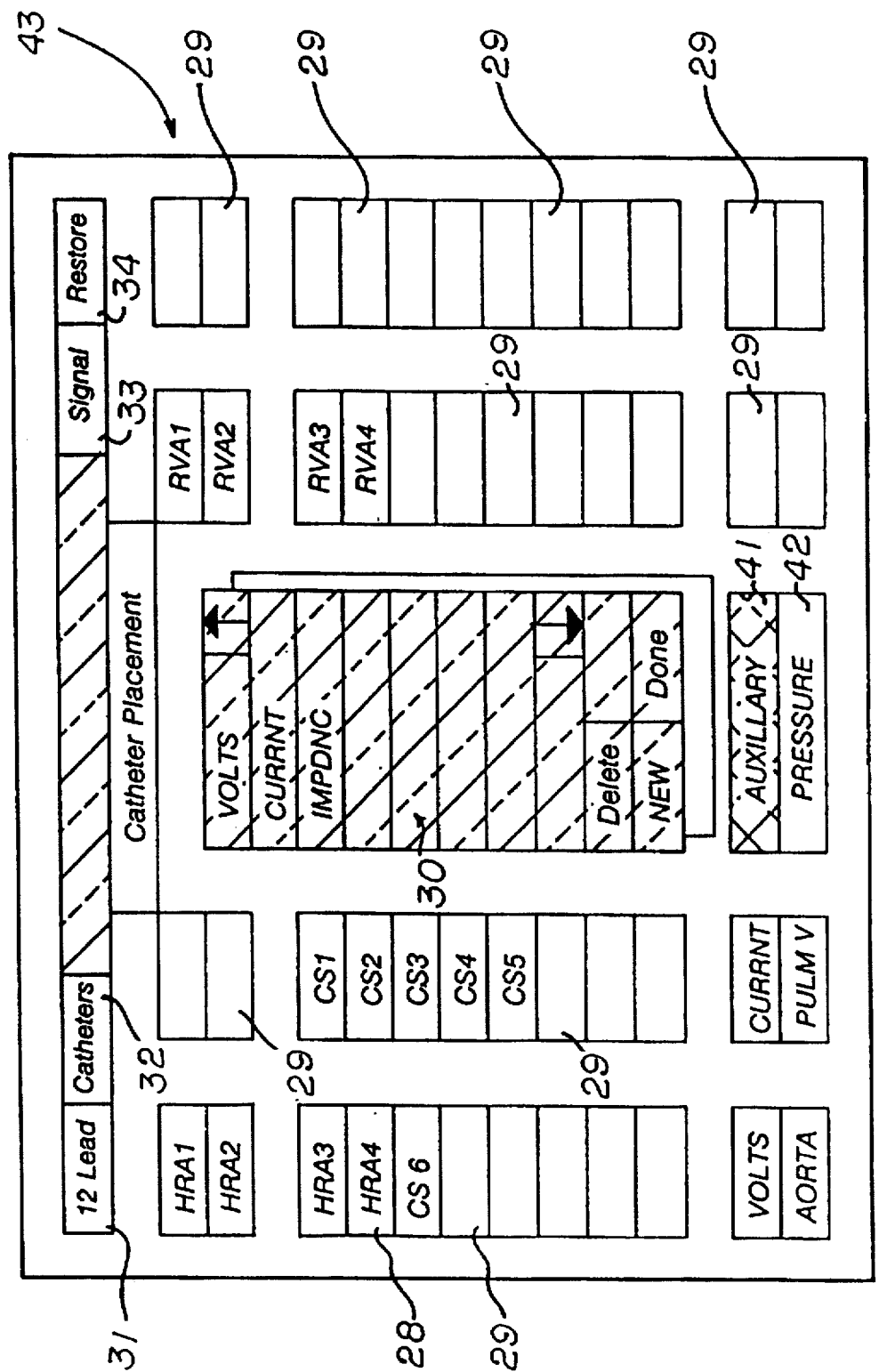

Briefly, to specify an input, the operator need only touch the key describing the input type, such as the intracardiac key 40, the auxiliary key 41, or the pressure key 42, then use the resulting directory 30 (See FIG. 4(b) to assign each label 28 to the field 29 that corresponds to the correct lead input connector 12, 13, 14, or 16. To quickly assign a multiple of fields 29 to a single label 28, the operator touches the desired label 28 in the directory 30, then touches as many fields 29 as desired. Operating in this fashion to assign labels is hereafter referred to as the Batch Edit Mode of operation. To make a single assignment of a label 28 to a field 29, the operator first touches the desired field 29 and then touches the desired label 28 in the directory 30. Assigning a single label 28 at a time in this fashion is referred to hereafter as the Single Edit Mode of operation.

In Batch Edit Mode, when the user chooses which field or fields 29 to apply the label 28 to by touching in succession each desired field 29, the plural leads of the catheter or sensor will be automatically numbered appropriately. The operator can continue in this way indefinitely. If a field 29 was empty prior to this operation, the field 29 will be filled in appropriately. However, if there was already a label 28 present in the field 29, all associated labels 28 will be updated with the new label 28 and each lead connector will be numbered appropriately. When the operator is finished with one label 28, another label 28 may be chosen. When all desired labels 28 are assigned, the operator chooses "Done" from the touch screen, in which case the directory 30 will disappear. If the operator selects a field 29 which cannot possibly be assigned (such as choosing a pressure field while entering the title "Intracardiacs") an error message will be presented.

If the operator chooses an empty field 29 directly from the catheter placement screen 43, the directory 30 will appear, immediately placing the operator in the Single Select Mode of the setup operation. When the operator then makes a label selection, the locations directory 30 disappears and the new information is displayed in the previously empty field 29.

To move a catheter label 28 in the Single Edit mode, the operator chooses ay one of the fields 29 containing the name of the catheter to be moved. All lead names of the catheter will then be highlighted, and the directory 30 will appear. The operator can then choose the new field 29 for the catheter, after which the directory 30 will disappear and the fields 29 will automatically be updated to show the new label 28.

Figure 4C:
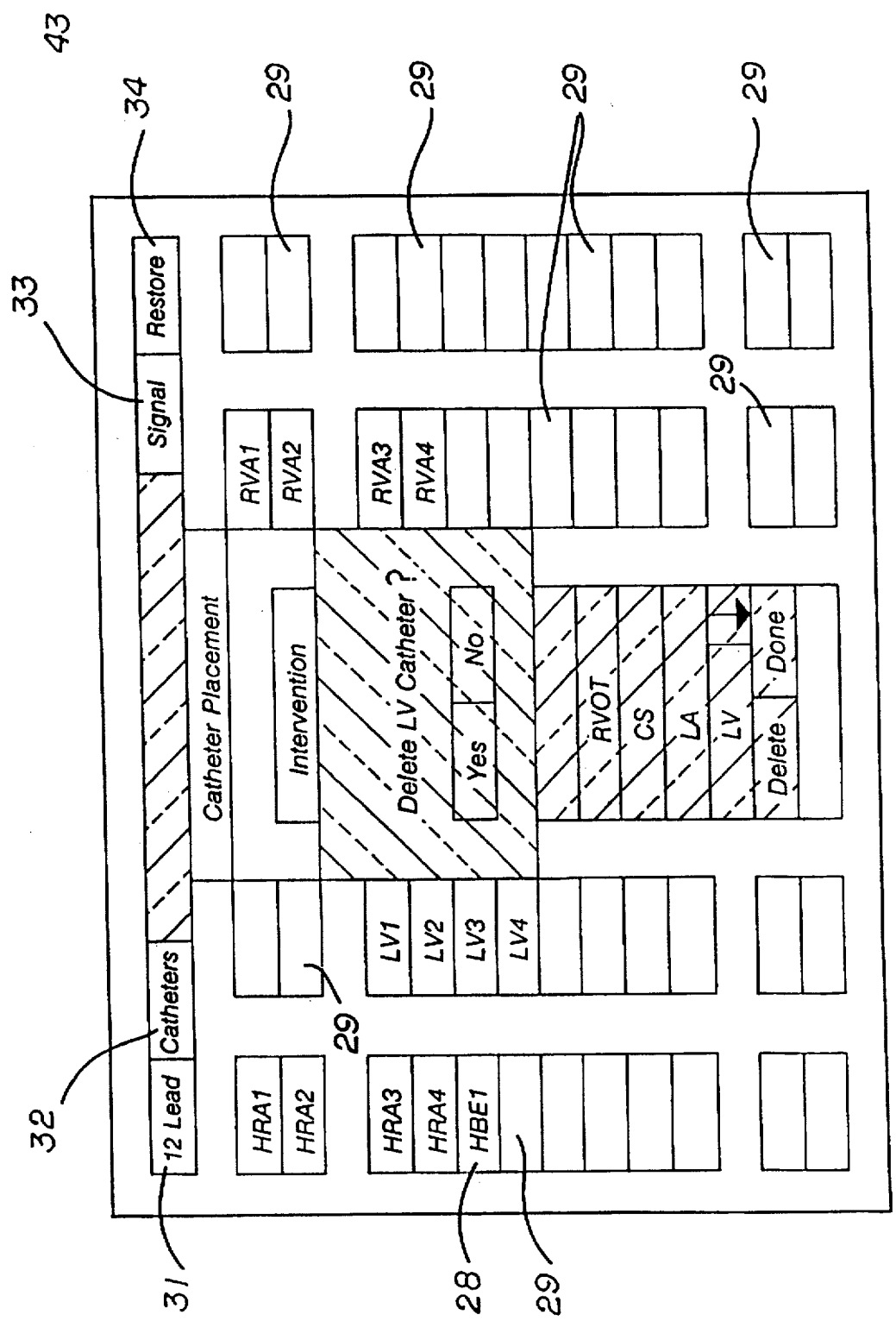

To remove a particular catheter in Batch Edit Mode, the user selects "Delete" from the directory 30 and then selects a field 29 associated with the particular catheter to be removed. As shown in FIG. 4(c), a popup containing the question "Delete XXXX Catheter?" will appear. If the operator selects "Yes", all leads of the associated catheter will be removed. If the operator selects an invalid field 29, such as an empty field or fields 29 from Pressure or Auxiliary input terminals 14 or 16, an error message will appear. In Single Select Mode, the operator will have first chosen the field 29 of interest, which will cause all similar fields 29 to be highlighted, then will choose "Delete" from the directory 30. All leads of the catheter will then be removed as well as the confirmation question and the directory 30.

Figure 4D:
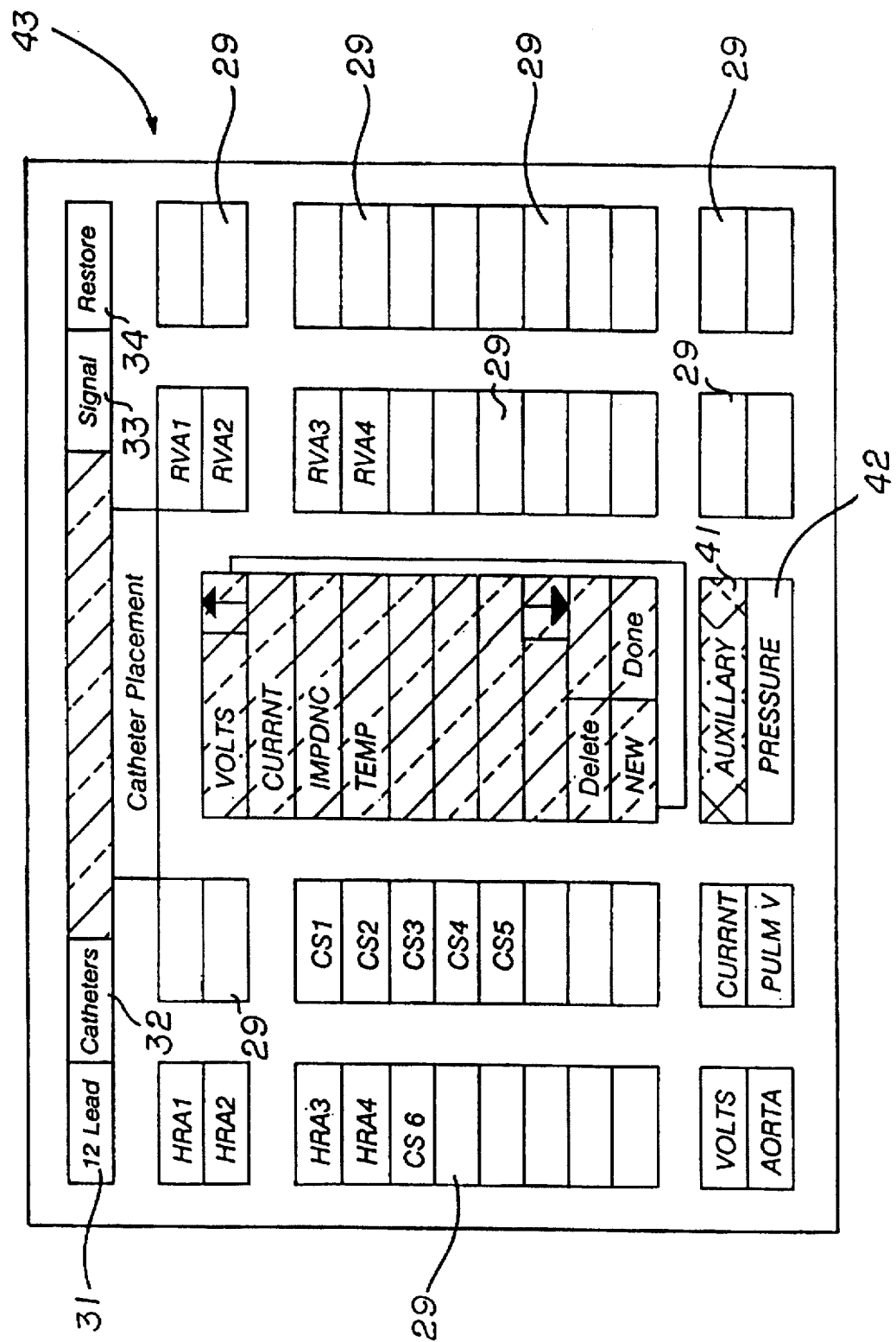

As shown in FIG. 4(d), the softkey "New" is available under the Auxiliary and Pressure directory 30 when in the Batch Edit Mode. When the "New" key is touched, it will be highlighted, and the directory 30 containing a keyboard popup will be presented. The operator may then type in the desired new label 28 and touch "Done" to save the entry to the directory 30. The operator may then select this label 28 for use as input channel label.

While working with the Auxiliary or Pressure channels, the softkey "Delete" will also remove a label 28 from the directory 30. To do so, the operator selects "Delete", which will be highlighted, and then chooses the desired label 28 from the directory 30. A question confirming the operator's intent will appear and the label 28 will be removed if the operator answers "Yes" to the confirming question.

Figure 4E:
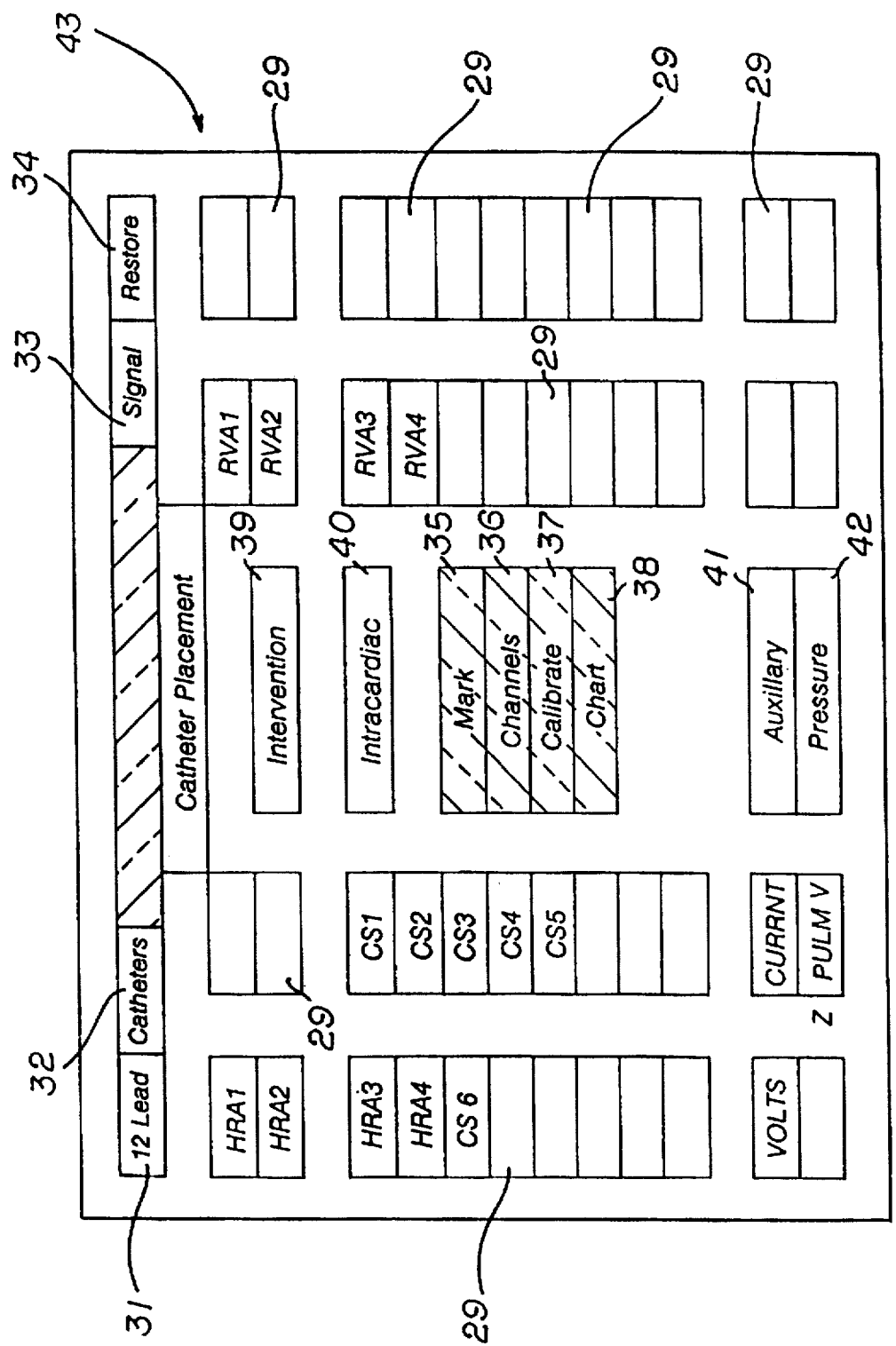

Zeroing of the Pressure channels 14 will also be available to the operator under the Pressure directory 30. The system 10 will zero a Pressure channel 14 upon request from the user. If in the Single Edit Mode, the pressure sensor will be open to atmosphere prior to touching the "Zero" softkey. The system 10 will then record the pressure signal for one second after the "Zero" key is touched and compute an offset value to be used to calibrate the channel. While zeroing is taking place the softkey will be highlighted. In the Batch Edit Mode, the operator chooses the "Zero" key and then choose the desired input to be zeroed. The field 29 will then be highlighted while zeroing is taking place. After completion, in either Batch or Single Edit Mode, the letter "z" will appear to indicate that the channel has been zeroed as shown in FIG. 4(e).

Figure 4F:
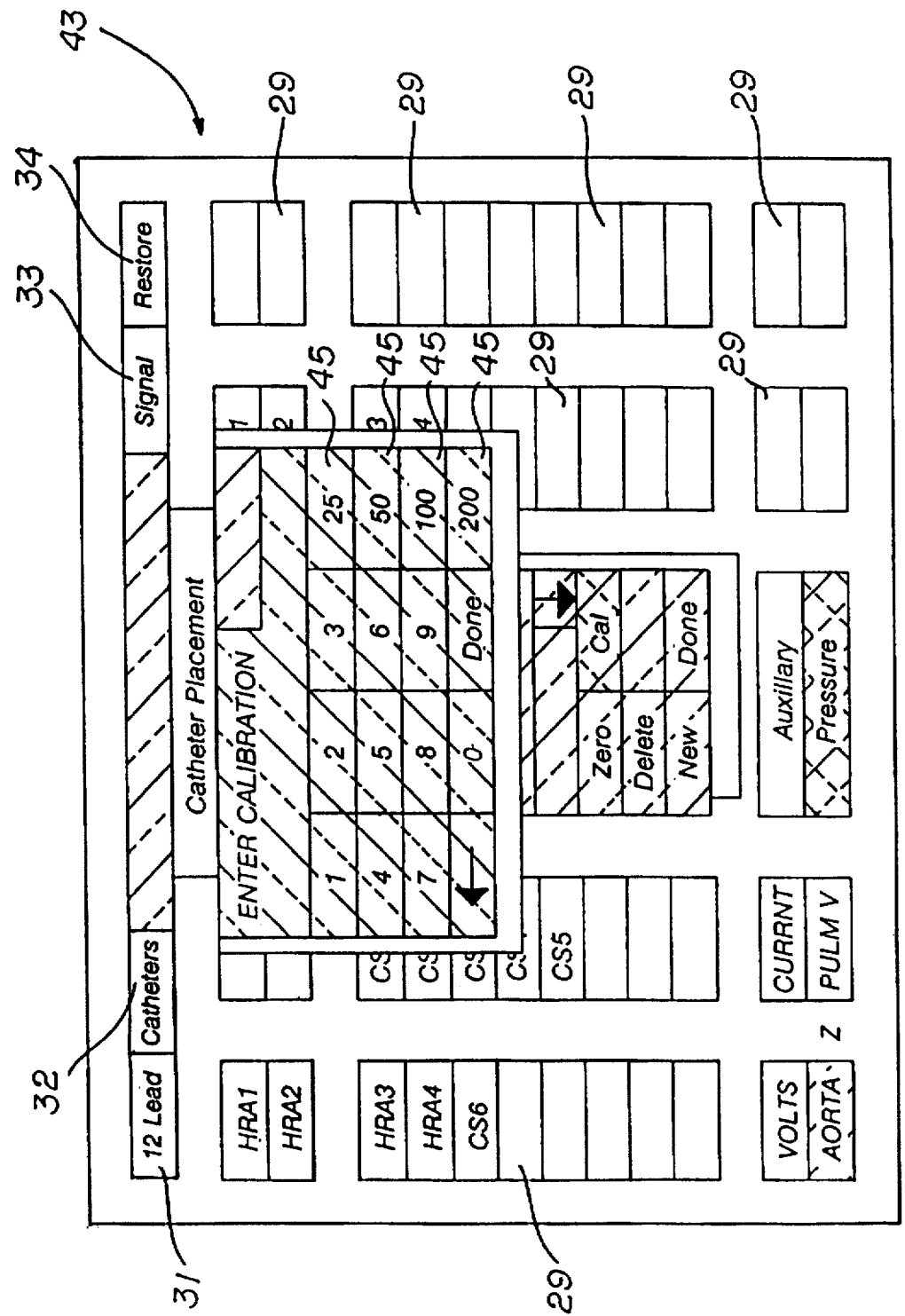
Figure 4G:
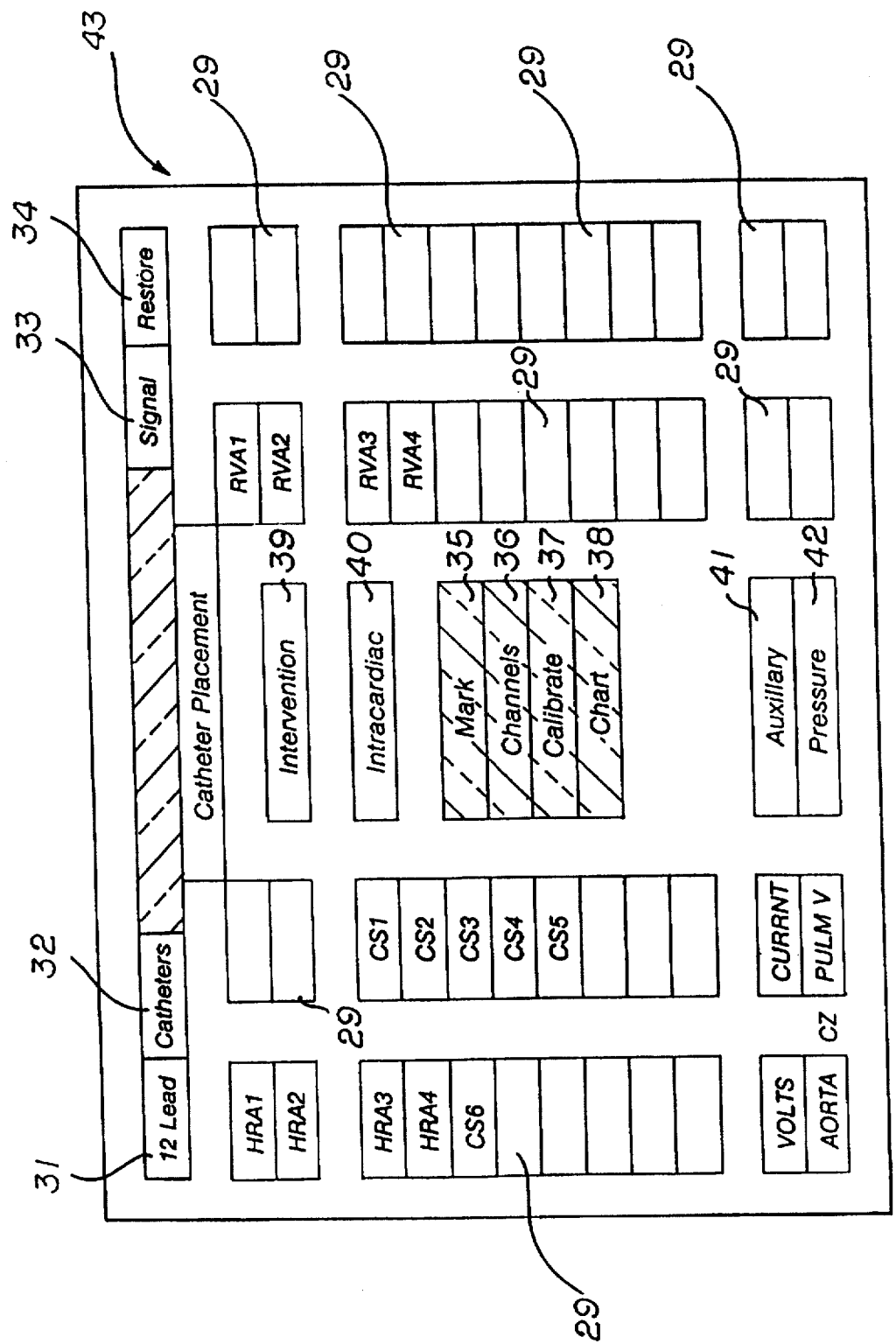

Calibration is available while setting up the pressure channels. The "Cal" key acts in a similar fashion as the "Zero" key as explained above. Once "Cal" has been touched, a numeric keypad directory 30 as shown in FIG. 4(f) will appear. The directory 30 will preferably contain four preprogrammed "Fast Cal" keys 45. The user then applies the calibrating pressure to the transducer and either enters the desired value or choose one of the "Fast Cal" keys 45. Once calibrated, a "c" will appear in the box beside the label 28 corresponding to the calibrated channel as shown in FIG. 4(g).

Signal Selection

To select the desired output parameters to be associated with each channel label 28, the operator selects the "Signals" Softkey. At this point as shown in FIG. 5(a), the second-of the two basic screens called the "Signals Screen" 44 will appear. The Signal Screen 44 contains a list of all assigned channels, their pole pairs, gains, filters, limiter level, and the output name of the channel which is to be used by the system 10 for display purposes.

The Signals Screen 44 will behave in a manner similar to the Catheter Placement Screen 43 described above. The signals screen 44 is preferably preprogrammed with the following soft keys: channel key 47, leads key 48, gain key 49, filter key 50, limiter key 51, and name key 52. Also, the twelve lead key 31, catheters key 32, signals key 33 and restore key 34 are preprogrammed on the Signals Screen 44 in the identical manner as the Catheter Placement Screen 43.

Figure 5B:
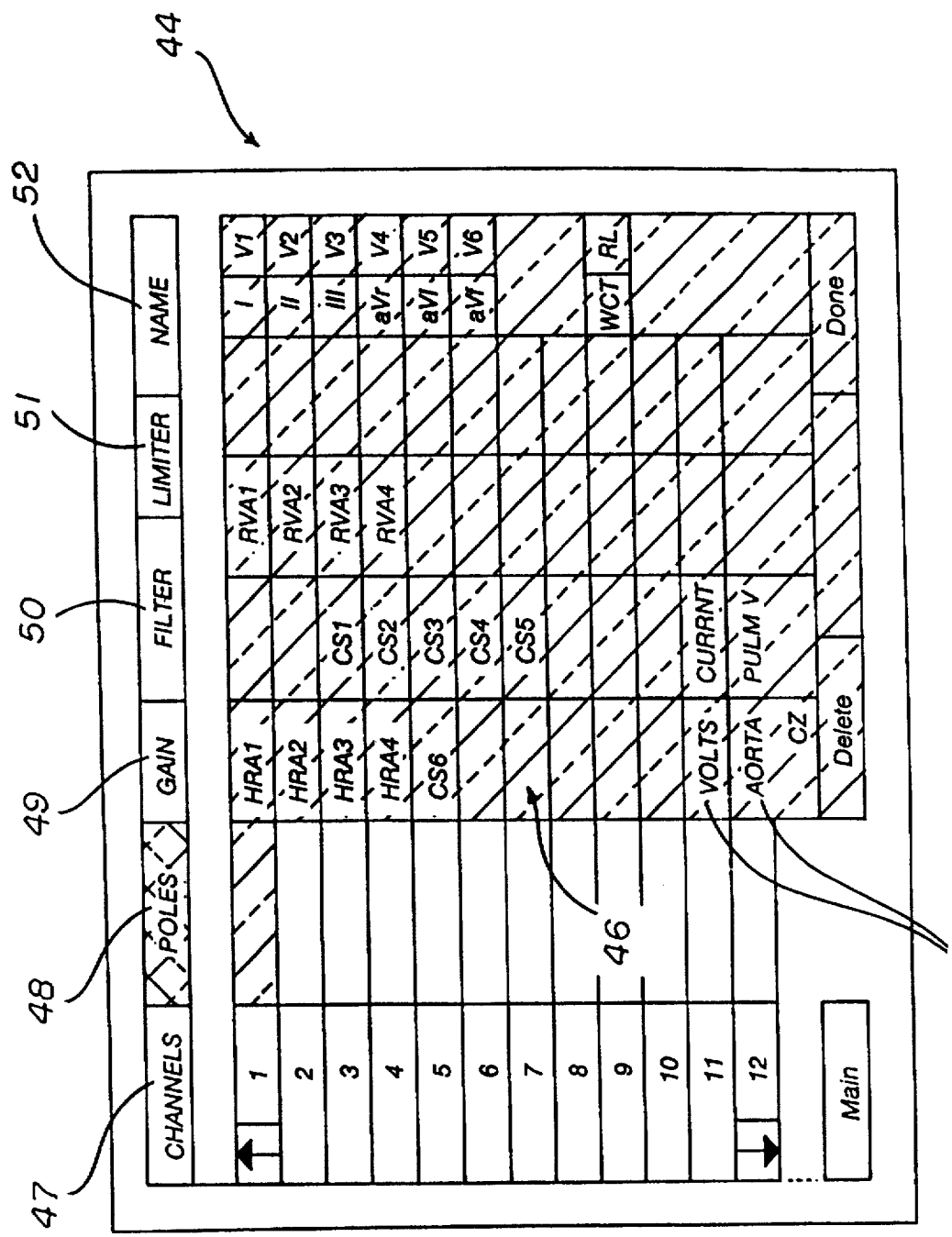

When a soft key is chosen, the operator is immediately placed in the Batch Edit Mode of the setup operation. As shown in FIG. 5(b), a small "Items" popup 46, displaying information relative to the chosen soft key will appear. The operator must then choose the particular item 53 or label 28 from the popup 46 desired to be used and then choose which field or fields 29 to apply it to. The operator can continue in this way indefinitely. When the operator is finished, "Done" can be chosen from the screen and the Items popup 46 will disappear. Alternatively, if the operator chooses one of the fields 29 directly, the field 29 will be highlighted, and the Items popup 46 will appear and place the setup operation into the Single Edit Mode. Once the operator selects the desired item 53, the Items popup 46 disappears.

At any time the operator can choose the "Catheters" key 32 from the Signals Screen 44 and return to the Catheter Placement Screen 43, if desired. Similarly, at any time in the Catheter Placement Screen 43, the operator can choose the "Signals" key 33 and return to the Signals Screen 44.

Output Channel Selection

To begin filling out the desired combination of leads for output from the system 10, the operator first touches the leads key 48. The Items popup 46 for Leads will appear as shown in FIG. 5(b) and contain a list of all available ECG, Intracardiac, Pressure and Auxiliary channels. Additionally, the ground leads "WCT" and "RL" will appear along with the softkeys "Delete" and "Done".

In Single Edit Mode the user will have previously chosen the desired field 29 to edit and can now choose the label 28 to use to complete an output channel. By touching the desired label 28, the label 28 will appear in the highlighted field 29 previously selected (ie. "RVA 1"). The operator's next touch will complete the lead pair and the label 28 therefore. If the completing pair is of similar type, then the label 28 will be automatically abbreviated to appear as a single prefix and a pair of lead numbers, such as "RVA 1-2". Otherwise the second half of the pair will just be appended and the label 28 will appear such as "RVA1-HRA1". When the operator selects an ECG, Auxiliary or Pressure channel, the label 28 will appear instantly. Once a pairing has been completed, the settings as previously indicated on the Signals Screen 44 associated with particular cardiac locations will be applied to the gain, filter, and limiter settings.

To edit the lead pair in Single Edit Mode, the operator touches the desired field 29 (which will be highlighted) and the Items popup 46 immediately appears. The operator then touches the desired new labels 28 from the Items popup 46. Of course, both labels 28 must e chosen again to complete the new lead pair.

To remove a label 28 in Batch Edit Mode, the operator chooses the softkey "Delete" from the Items popup 46. This will be highlighted and the operator then chooses the desired label 28. The label 28 will be removed from the screen as well as all other information for that channel. "Delete" will unhighlight after being used once. In Single Edit Mode the desired label 28 will already be highlighted and will be removed once "Delete" has been touched.

Gain and Filter Selection

The gains and filters are pre-set to default values which can be changed by the operator if desired. To change the default gains or filters, the operator touches the desired gain key 49 or filter key 50, and an Item popup 46 appears as shown in FIG. 5(c) with all available gains or filter settings respectively. In Single Edit Mode, the operator will have previously chosen the field 29 to be edited and can now select the new item 53 from the presented list. The Item popup 46 will then disappear. In Batch Edit Mode the operator first selects the item 53 desired from the Item popup 46 and then selects all fields 29 it is desired to apply it to. The operator may continue in this manner until "Done" is finally selected. While adjusting filter settings, more than one item 53 may be chosen by the operator. These items 53 include High, Low and Notch filter settings. Each item 53 is highlighted as it is touched to indicate which items 53 have been chosen. If more than one item 53 in a particular section is touched, the highlight moves to the new item 53.

Limiter Setting

Figure 5D:
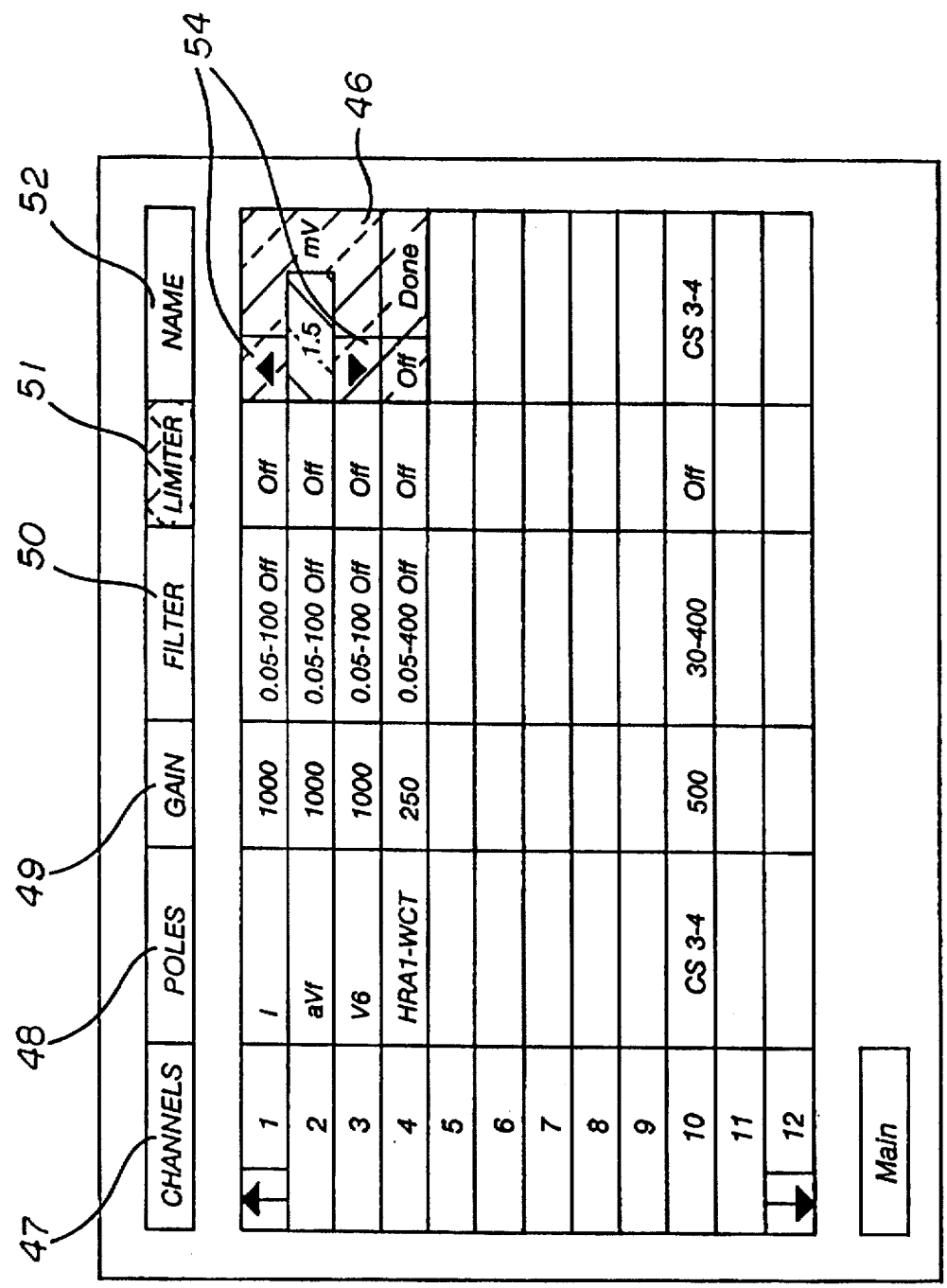

As shown in FIG. 5(d), the Limiter setting Items popup 46 presents a sliding scale to indicate the relative amount of limiting. To adjust the limiter setting, the operator touches the direction arrows 54 to choose the desired amount. The numbers placed in the appropriate filed 29 on the Signals Screen 44 corresponding to the limiter reflect percentages of full scale. In Single Edit Mode there is a "Done" key on the popup 46 for the operator to indicate when the current level is correct. In Batch Edit Mode, the operator selects the amount of limiting and then applies it to the desired field or fields 29. "Done" is used to indicate when the operator has finished applying new limiting levels to all the desired channels. Limiting is applied in a bipolar fashion and is a ± limit.

Name Selection

Every channel preferably includes a name. The name fields are filled out with predetermined default names as the lead pairs are formed, the default name being the same as the label 28. However, the user can edit the name using the keyboard presented in the Name Selection popup 46, as shown in FIG. 5(e). Once completed, the operator can select "Done" and the keyboard popup 46 will disappear. In Batch Edit Mode, the operator types in the desired name and then chooses the desired field 29. Whatever is in the keyboard buffer 55 at the time the operator touches the desired field 29 will be used as the name. The operator then touches "Done" to remove the popup 46 and exit Batch Edit Mode. Single Edit Mode is operated in a similar manner according to the general format explained above for single edit mode operation.

Channel Number Editing and Channel Deletion

Figure 5F:
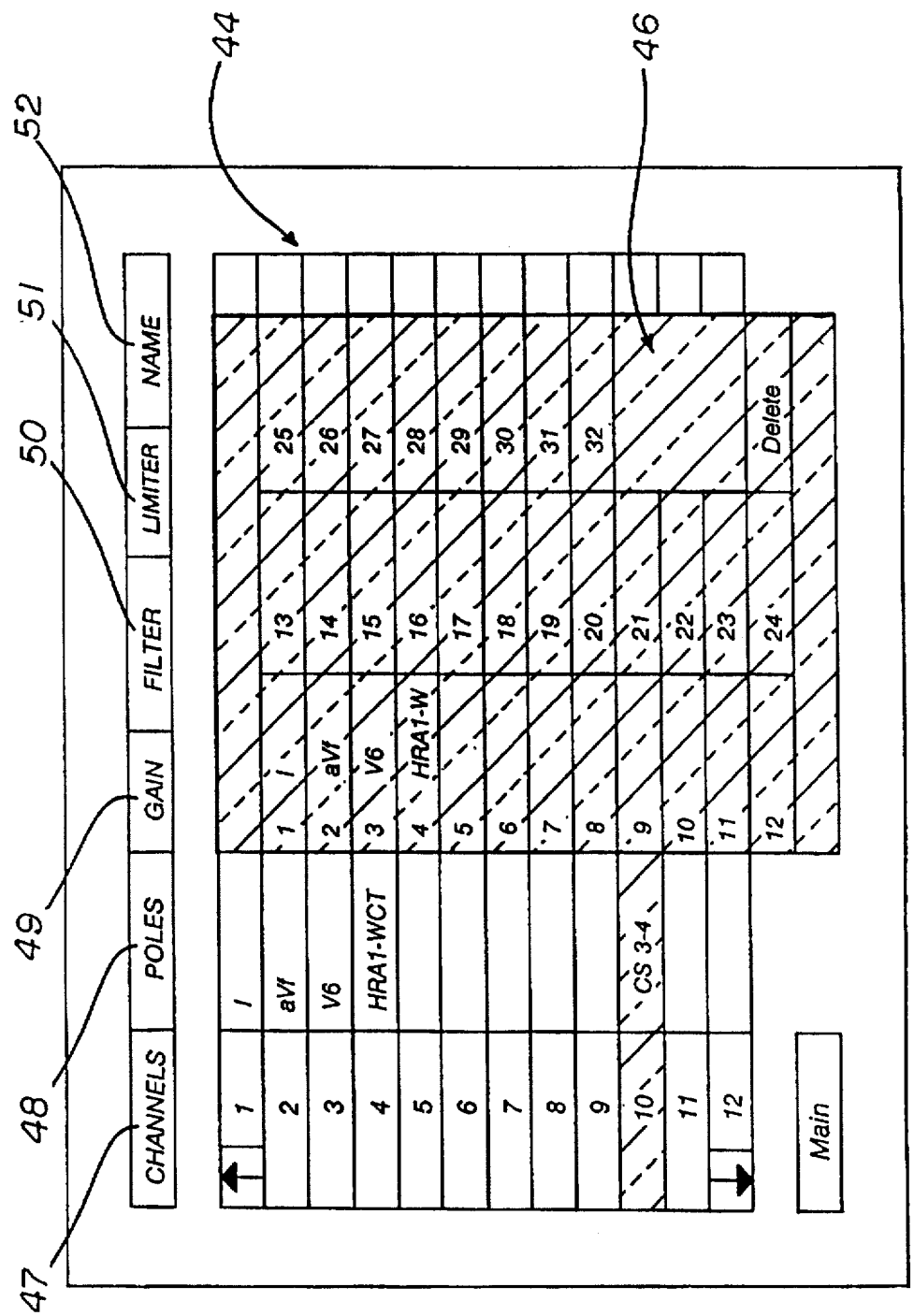

Channel editing will only take place in Single Edit Mode. As shown in FIG. 5(f) the operator selects the desired channel number to edit and the Items popup 46 appears with all the channels and their names, and the selected channel number is highlighted. Upon choosing a new channel which is not already in use, the popup 46 will disappear and the channel will be moved to it's new position. The old position is initialized to an unused channel. If the operator selects a channel position from the popup 46 which is already occupied, the popup 46 will disappear, and the two channels will swap their configurations.

To remove a channel the operator selects "Delete" from the popup 46 and the previously selected channel will be removed.

An example of a completed Signals Screen 44 is shown in FIG. 5(g).

Catheter Placement Name Area

Figure 6A:
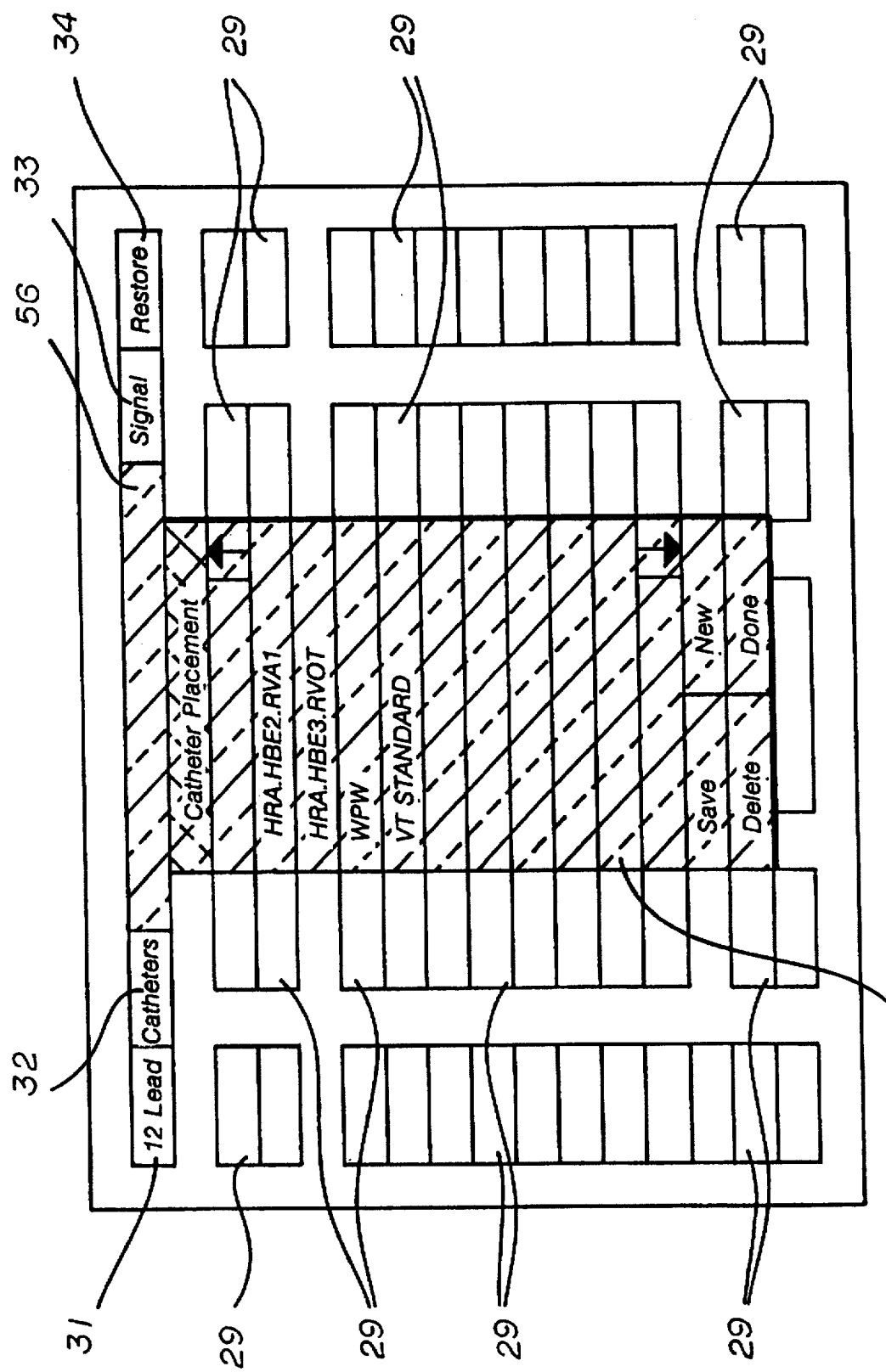
Figure 6B:
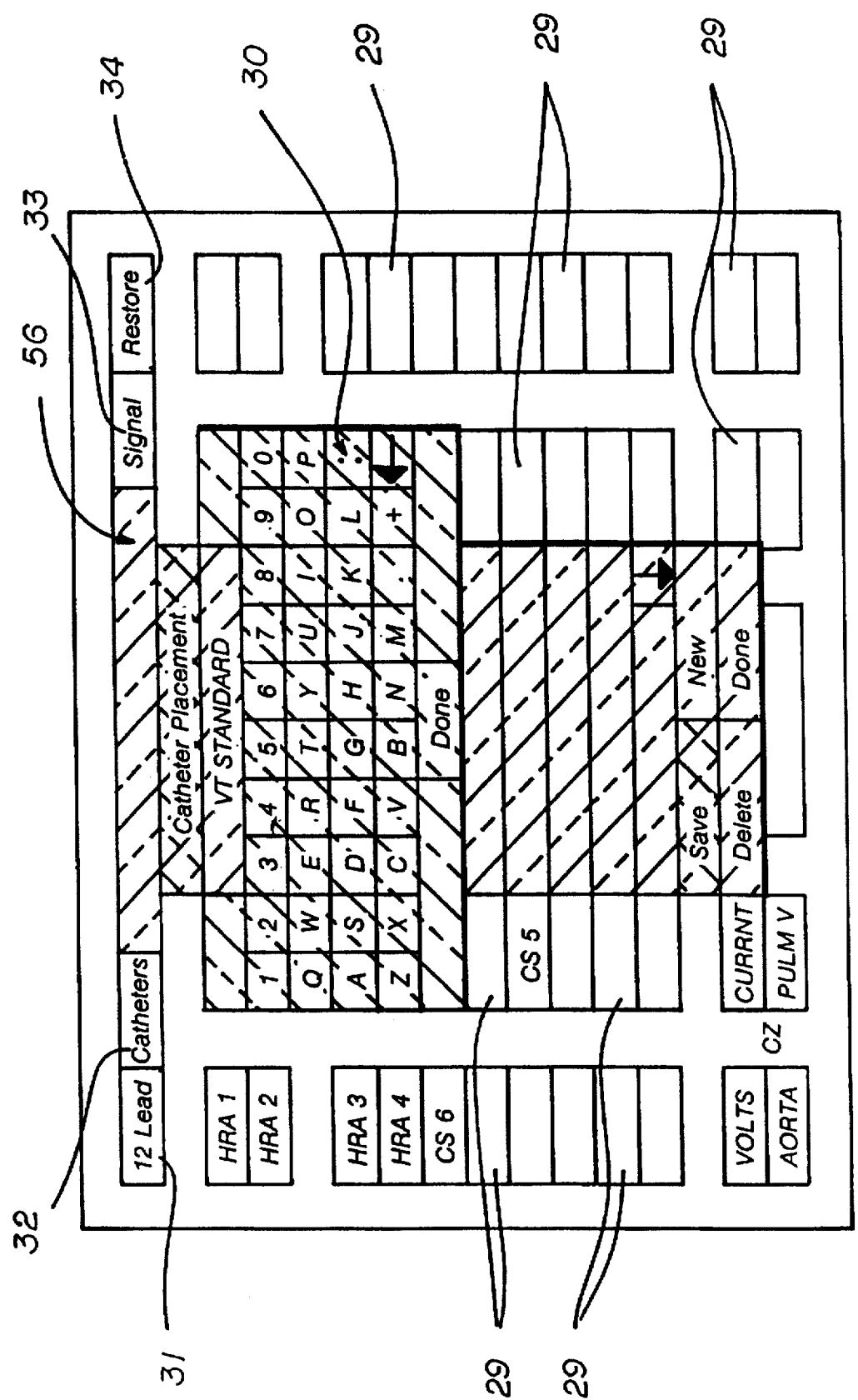

Referring again to the Catheter Placement Screen 43, as shown in FIG. 6(a), the "Catheter Placement Name" area 56 not only displays the currently invoked catheter placement name but is also active to the touch. Once the operator has completed preparations of the system 10 for an electrophysiological procedure, the entire setup may be saved for recall later. To do this the operator simply touches the "Catheter Placement Name" area 56. If there is already a setup invoked, that setups name will be present in the area 56, otherwise the word "Setup" will appear. The operator is then presented with the directory 30 containing a list of all available preset catheter setups as well as the softkeys "New", "Delete", "Save", and "Done". Upon selecting "Save" the operator is presented with the keyboard directory 30 as shown in FIG. 6(b) and is prompted to fill in the name of the current setup. If a previous catheter placement had been invoked, the operator is prompted to overwrite the old one or to create a new name. "Save" will be highlighted while active. The catheter placement setup will be saved both to the system 10 memory and the computer processing unit if attached. To finish saving the operator selects "Done" from the keyboard directory 30.

Figure 6C:
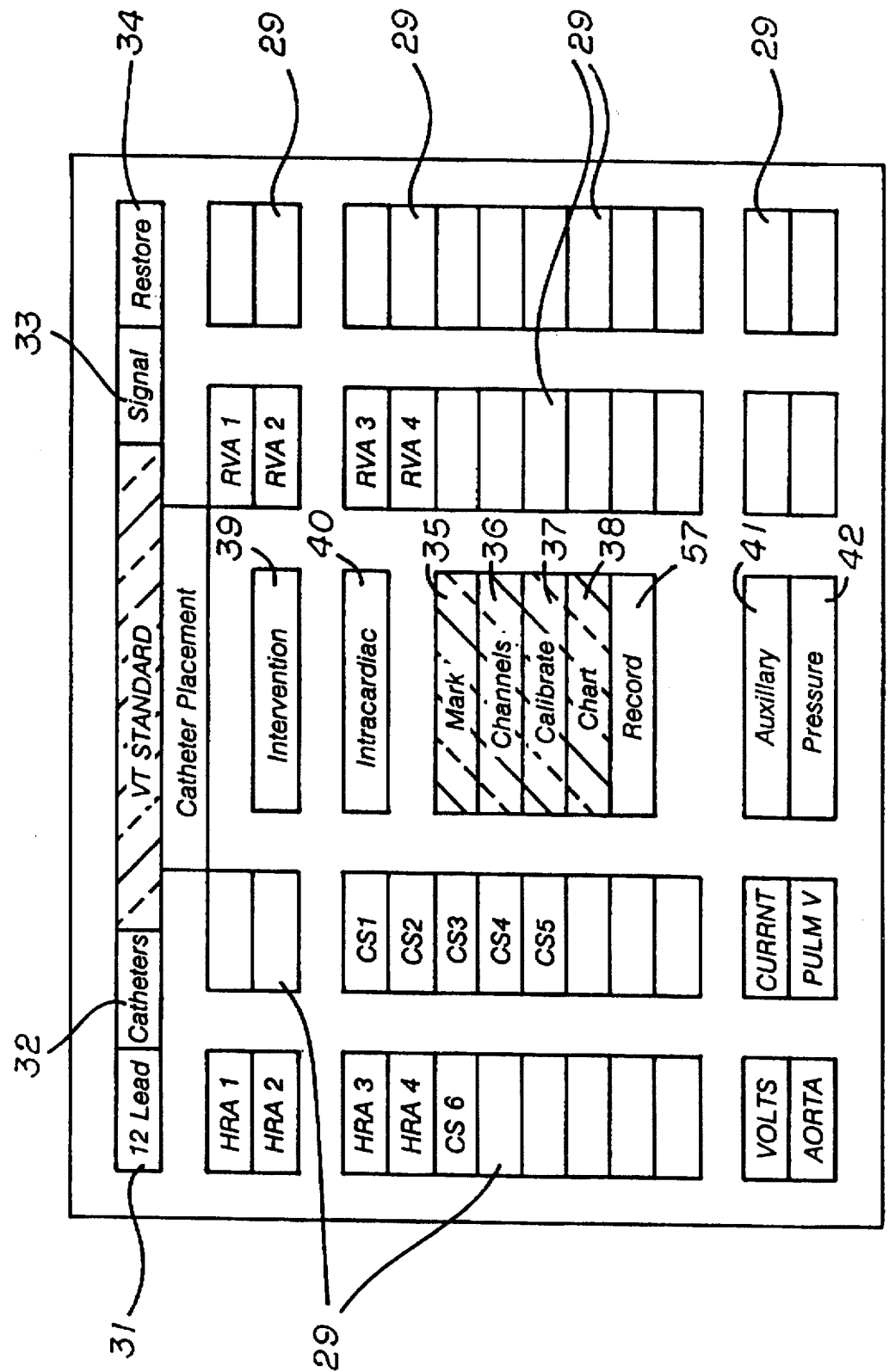

To invoke an old catheter placement the user touches the "Catheter Placement Name" area 56 and is presented with the directory 30 containing the list of currently stored catheter setups as again shown in FIG. 6(a). The operator then chooses the desired catheter setup by touching the desired name on the directory 30. The Catheter Placement Screen 43 will then be filled with that catheter setups' configuration such as shown in FIG. 6(c). If this is the correct catheter setup, the operator selects "Done" and the directory 30 disappears and the hardware is automatically reset with the new catheter setup configuration.

To remove a catheter setup configuration, the operator again initiates the catheter placement directory 30 and chooses "Delete". The operator then selects the setup to be removed, and the system 10 asks for confirmation. Upon answering "Yes", the setup is removed. To return to normal operation the operator selects "Done".

To initialize the Catheter Placement Screen 43, the user selects "New" which will clear all inputs and uninvoke the current catheter setup.

Twelve Lead Softkey and Restore Softkey

The "Twelve Lead" softkey 31, and the "Restore" softkey 34 are preferably located on opposite sides of the Catheter Placement Name area 56 on the Catheter Placement Screen 43 as shown in FIG. 6(a).

By touching the "Twelve Lead" softkey 31 the operator can toggle the first twelve outputs of the output terminals 17 to receive all twelve ECG leads attached at the input ECG terminal 11. A directory 30 indicating that the twelve Lead ECG is being acquired will appear. The directory 30 contains a softkey containing the previous catheter placements name. To return to the previous placement the operator touches this softkey. If the placement has not yet been named, the softkey will contain "Return".

The "Restore" softkey 34 is used in the case that signals have drifted off of the computer display monitor on the chart recorder, either from movement of the patient or from a defibrillation, and the operator wishes to remove the DC offset and place the signals back into the middle of the monitor. The Restore key 34 will be highlighted for appropriately one second to indicate that the signal placement is automatically being done.

Mark Softkey

The "Mark" key 35 is used to mark specific events in time during an electrophysiology procedure. "Mark" will be highlighted for appropriately one second after it is pressed to indicate to the operator that the mark is automatically being placed in the time record.

Calibrate Softkey

The "Calibrate" key 37 is used to send a square wave of 1 mV.5 Hz (RTT) to all channels. Once pressed the key will be highlighted. To stop the calibration pulse the operator presses Calibrate key 37 again and the calibration stops. The highlight will also be removed.

Record Softkey

The "Record" key 57 is used to initiate storage of data. Recording will start from five seconds previous to when the record key 57 is touched, and storage thereafter is continuous. The operator will be able to stop storage by touching the record key 57 again.

Chart Softkey

The "Chart" key 38 delivers a TTL level to the chart recorder if attached to the system. While active, the "Chart" key 38 will remain highlighted. To stop the chart recorder, the operator simply presses Chart key 38 again.

Automatic DSP Calibration

Figure 7:
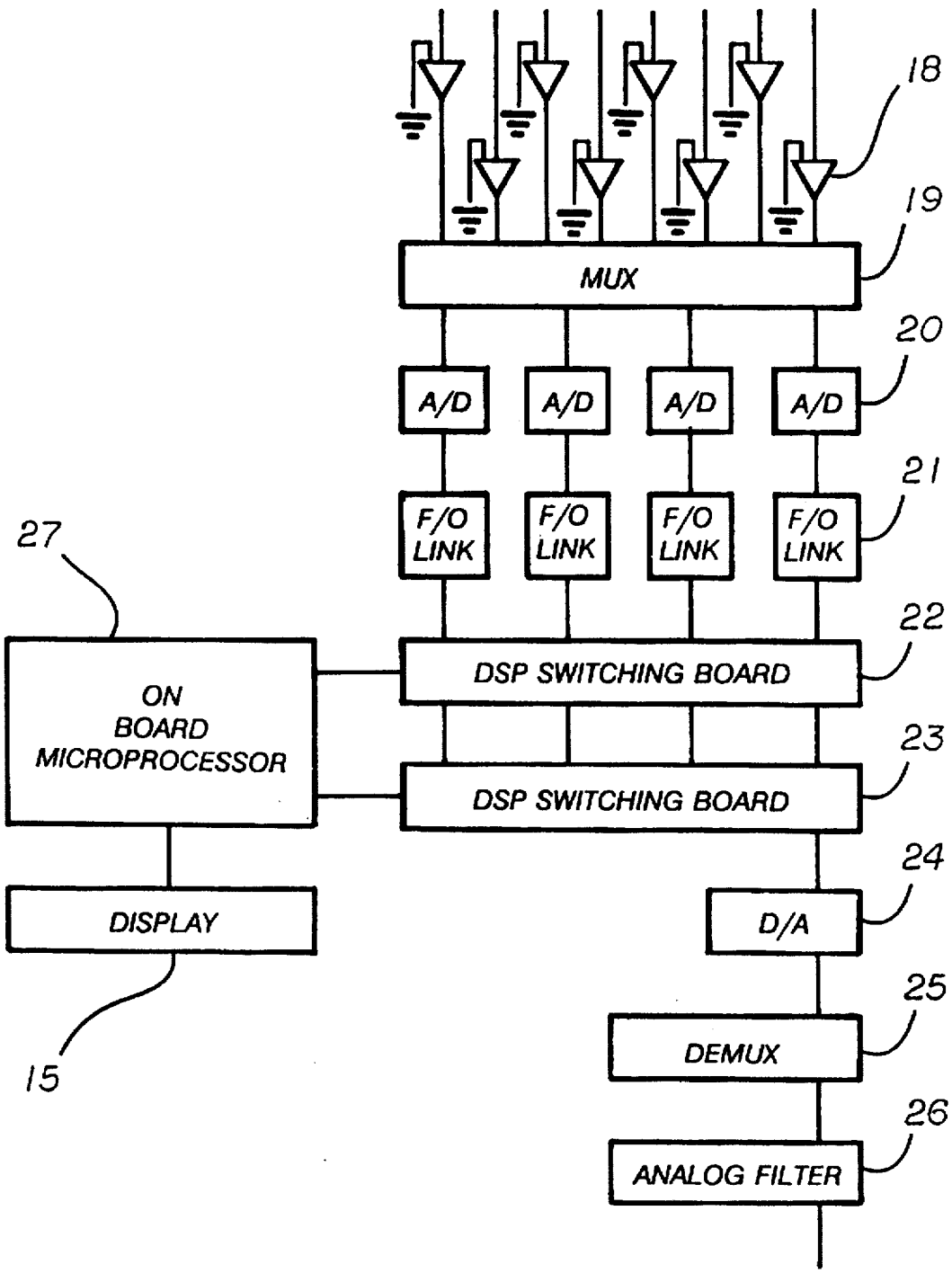
FIG. 7 is a block diagram of the internal electronics of the preferred embodiment of the integrated electrical signal switching and amplifying system.

Referring now to FIG. 7, if the gain or phase response of the front-end amplifiers 18 are not identical, then the digital signal processor (DSP) 22 will not eliminate all of the common mode signal during the common mode signal rejection operation. Therefor, an automatic calibration system is included in the system 10 of the present invention to automatically digitally calibrate the front-end amplifiers 18 prior to the initial use of the system 10 in order to correct for any nonuniform phase or gain performance between the front-end amplifiers 18.

The automatic calibration is performed by attaching a cable (not shown) from the output channels 17 to all of the Intracardiac input channels 12 in parallel. The operator then enters the "Calibration Mode" of the system 10 and the DSP 22 automatically enters a known signal at each input channel 12 through the attached cable.

The DSP 22 then samples the gain and phase of the signal it receives from each of the front-end amplifiers 18. The difference between the gain and phase value of the known signal and the gain and phase value of the signal as received by the DSP 22 after passing through each front-end amplifier 18 is then digitally stored by the system 10 in a table. Thereafter, during normal (non-calibration mode) operation of the system 10, each signal received by the DSP 22 from the front-end amplifiers 18 is corrected by the stored digital value corresponding to the difference between the known calibration mode signal and the received signal of each front-end amplifier 18. In this manner, any common mode signal received into the DSP 22 will be completely rejected regardless of which inputs 12 are used.

Since the automatic calibration values are stored digitally in a table in the system 10, they do not experience any significant drift over the normal life of the system 10. Calibration of the front-end amplifiers 18 therefore is intended to be necessary only as an initial calibration, i.e. one time calibration before initial use of the system 10. Since this automatic calibration need be performed only once, it can be performed by the manufacturer of the system 10 and the subsequent operator will have no need to be concerned with it during normal use.

OPERATION

The block diagram of FIG. 7 shows the architecture of the most important internal electronics of the present invention. Up to sixty-four electrical inputs from the input terminals of the system 10 are passed through front-end amplifiers 18 and directly into a multiplexer 19. The signals are multiplexed into four output channels carrying sixteen input channels each and passed through A/D converters 20 and fiberoptics links 21 into the DSP switching board 22. The DSP 22 operates as a switching matrix, such as in the manner of prior art analog switching matrixes, except that instead of switching analog signals electronically into differential amplifiers, the DSP 22 of the present invention switches digital signals and operates itself as a "differential amplifier". This is done by electronically combining the digital representations of each signal, such as by subtraction, which results in sixteen output channels (or thirty-two output channels if desired) which pass directly into a DSP processing board 23 (or two DSP processing boards in the case of thirty-two channel outputs from the DSP switching board 22).

As is readily evident, the DSP switching board 22 of the present invention has been configured for operation to eliminate common mode signals from raw, digitized analog input signals. In this manner, the present invention is distinguished from any prior art use of digital signal processors since common mode signal noise is removed by prior art systems before any digital signal processors are utilized. The prior art use of digital signal processors has been simply to process signals which have previously been passed through an analog witching matrix. In these prior art systems, the common mode rejection function on the analog signals has already been performed through known techniques using differential amplifiers. In the present invention however, the DSP switching board 22 itself operates as a differential amplifier to perform the signal switching operation and to do common mode rejection on the raw digital signals.

The signals received by the DSP processing board 23 are processed for gain, signal limiting and the application of a plurality of filters thereto. Each DSP processing board 23 (one in the case of sixteen output channels from the DSP switching board 22, and two in the case of thirty-two output channels from the DSP switching board 22) outputs a single multiplexed channel to a D/A converter 24 which is then passed through a de-multiplexer 25 to restore sixteen channels. These are then passed through an analog filter 26 to the output 17 of the system 10.

The DSP switching board 22 and DSP processing board or boards 23 are driven by an onboard microprocessor 27 which is also operationally attached to the display 15.

In constructing the system 10 of the present invention using the DSP switching board 22, a large amount of bulk is eliminated therefrom, thus allowing the system 10 to be significantly reduced in size compared to prior art hardware.

Also, the utilization of the DSP processing board 23 for filter, limiter, and gain application significantly aids in downsizing the overall physical dimensions of the system 10 by allowing elimination of the prior art type filter blocks which commonly include five different capacitors and an analog switch for each signal channel. The result is a system 10 which is significantly smaller than prior art hardware and which is therefore conveniently positionable directly at the patient's bedside to allow bedside control of the system 10 by the operator during setup and electrophysiology procedures.

The system 10 of the present invention can be attached through its output ports 17 by a cable to a computer processing unit, analog monitor, and/or chart recorder. An example of a computer processing unit usable with the system 10 of the present invention is manufactured by Quinton Electrophysiology Corp. of Markham, Ontario, Canada, and is presently being marketing under the trademark "EPLab".

Since the DSP switching board 22 is used for common mode rejection, it is very advantageous in the present invention to employ A/D converters having very high resolution, such as sixteen bit resolution.

The preferred gain ranges for the system 10 include gain ranges of 100 to 5000 for ECG, intracardiac and pressure channels, and gain ranges between 1 and 5000 for the auxiliary channels. The system 10 employs three different filters, including high pass filters in the range of DC, 0.05 Hz, 1.0 Hz, 10 Hz, and 30 Hz, low pass filters in the range of 40 Hz, 100 Hz, 200 Hz, and 400 Hz, and notch filters in the range of 50 or 60 Hz. The common mode rejection level is preferably set at greater than 100 DB.

It will be apparent from the foregoing that, while particular embodiments of the invention have been illustrated and described, various modifications can be made thereto without departing from the spirit and scope of the invention. Accordingly, it is not intended that the invention be limited, except as by the append claims.

We claim:

1. An integrated electrical signal switching and amplifying system for receiving intracardiac electrical signals from a patient, amplifying the intracardiac electrical signals from the patient, switching the amplified intracardiac electrical signals, and outputting the switched intracardiac electrical signals, said system comprising:

- at least one electrical signal receiver for receiving intracardiac electrical signals from a patient,
- at least one electrical signal amplifier for amplifying the intracardiac electrical signals received from the at least one electrical signal receiver,
- at least one analog to digital converter for converting the amplified intracardiac electrical signals received from the amplifier into digital signals,
- at least one digital signal processor for performing at least one signal switching operation on the amplified digital intracardiac electrical signals received from the converter,
- at least one electrical signal output for outputting the switched intracardiac electrical signals received from said processor, and
- means for visual review of the switched intracardiac electrical signals from the at least one electrical signal output.

2. A system according to claim 1 wherein said at least one electrical signal receiver includes means for receiving analog intracardiac electrical signals, and said at least one electrical signal amplifier includes means for converting the analog intracardiac electrical signals to digital intracardiac electrical signals associated therewith and said at least one digital signal processor further includes means for removing common mode signal noise from the digital intracardiac electrical signals.

3. A system according to claim 1 further including a microprocessor, said at least one digital signal processor being operatively interconnected with and controlled by said microprocessor at a location adjacent to the patient.

4. A system according to claim 1 further including a microprocessor which is operatively interconnected with and controls said digital signal processor from a location adjacent to the patient; a separate processing unit at a location remote from the patient which is operatively interconnected with and controls said digital signal processor; and
- an interactive display interconnected with said microprocessor and which allows operator control of said microprocessor therefrom.

5. A system according to claim 1 wherein said at least one digital signal processor further includes means for performing signal filtering operations on the amplified digital intracardiac electrical signals switched by said at least one digital signal processor.

6. A system according to claim 1 wherein said at least one electrical signal receiver includes a plurality of input terminals for receiving intracardiac electrical signals from one or more catheters interconnected therewith and said at least one electrical signal output further includes means for outputting information related to the position of the one or more catheters in the body of the patient and said plurality of input terminals receiving the intracardiac electrical signals from the one or more catheters therethrough.

7. A system according to claim 6 wherein said system further includes a microprocessor having means for receiving and storing information related to the position of said one or more catheters in the body of the patient and the intracardiac electrical signals via said plurality of input terminals.

8. A system according to claim 7 wherein said microprocessor includes means for storing a plurality of setup formats for identifying the positions of the one or more catheters interconnected to said plurality of input terminals and for receiving intracardiac electrical signals from the one or more catheters.

9. A system according to claim 7 further including a display means for displaying labels assigned to said plurality of input terminals.

10. A system according to claim 1 wherein said at least one electrical signal receiver further includes a plurality of electrical signal receivers for receiving intracardiac electrical signals from intracardiac catheters, a plurality of electrical signal receivers for receiving ECG electrical signals from ECG leads, and at least one electrical signal receiver for receiving pressure electrical signals from at least one pressure sensor.

11. A system according to claim 1 wherein said at least one digital signal processor is a differential amplifier and performs said at least one signal switching operation on the amplified digital intracardiac electrical signals.

12. A system according to claim 1 further including means for calibrating and wherein said at least one electrical signal amplifier includes a plurality of front-end amplifiers therein and said means for calibrating operates to correct for gain and phase performance variations between said plurality of front-end amplifiers of said at least one electrical signal amplifier.

13. A system according to claim 12 wherein said means for calibrating further includes means for determining and storing digital calibration values associated therewith and wherein said digital calibration values correspond to the difference between the gain and phase values of a known calibration signal and the gain and phase values of the known calibration signal as received by said at least one digital signal processor after the known calibration signal has passed through said plurality of front-end amplifiers.

14. A system according to claim 13 further including means for applying said digital calibration values to the amplified digital intracardiac electrical signals received by said at least one digital signal processor from said front-end amplifiers wherein the amplified digital intracardiac electrical signals received by said at least one digital signal processor are altered using the digital calibration values to correct for gain and phase performance variations between each of said plurality of front-end amplifiers.

15. An integrated intracardiac signal switching and amplifying system for receiving intracardiac signals from the body of a patient, amplifying the received intracardiac signals, switching the amplified intracardiac signals, and outputting the switched intracardiac signals, said system comprising:
- an intracardiac signal receiver for receiving the intracardiac signals from a patient,
- an intracardiac signal amplifier for amplifying the received intracardiac signals,
- an analog to digital converter for converting the amplified intracardiac signals into digital intracardiac signals,
- a digital signal processor for performing a signal switching operation on the digital intracardiac signals, and
- an intracardiac signal output for outputting the switched intracardiac signals.

16. A system according to claim 15 wherein said signal receiver receives analog intracardiac signals from the body of a patient, and said signal amplifier converts the analog intracardiac signals to digital intracardiac signals and said digital signal processor further performs a common mode signal noise operation on the digital intracardiac signals.

17. A system according to claim 15 wherein said signal receiver includes a plurality of input terminals and said signal output further includes means for outputting information related to the origination of the intracardiac signals received via said input terminals.

18. A system according to claim 17 further including a microprocessor having means for receiving and storing information related to said input terminals and for receiving intracardiac signals.

19. A system according to claim 18 wherein said microprocessor includes means for storing a plurality of setup formats identifying the positions of catheters connected to said input terminals.

20. A system according to claim 15 wherein said signal receiver includes a plurality of intracardiac signal receivers for receiving electrical signals from intracardiac catheters, a plurality of ECG signal receivers for receiving electrical signals from ECG leads, and at least one pressure signal receiver for receiving electrical signals from at least one pressure sensor via said input terminals.

21. A system according to claim 20 wherein said signal receiver includes a plurality of input terminals and said signal output further includes means for outputting information related to the origination of said intracardiac and pressure signals via said input terminals.

22. A system according to claim 20 further including input terminals for receiving electrical signals from stimulation and lesion generating cardiac catheters.

23. A system according to claim 15 wherein said signal amplifier further includes a means for calibrating and said means for calibrating operates to correct for gain and phase performance variations between said amplifier and the phase and gain of a known signal.

24. A system according to claim 23 wherein said means for calibrating includes storage means for storing digital calibration values in said said storage means and wherein said digital calibration values represent the difference between the gain and phase values of a known calibration signal and the gain and phase values of said known calibration signal as received by said digital signal processor after said known calibration signal has passed through said amplifier and is received by said digital signal processor.

25. A system according to claim 23 including means for automatically applying said stored digital calibration values to signals received by said digital signal processor from said amplifier such that said signals received by said digital signal processor are digitally calibrated to correct for gain and phase performance variations caused by said amplifier.

26. A method for processing an intracardiac signal from a patient with an integrated signal and amplifying system for use in an electrophysiology procedure, the method including:

receiving an intracardiac signal from the patient with a received, amplifying the intracardiac signal received by the receiver with an amplifier to create an amplified signal, converting the amplified signal received from the amplifier with an analog to digital converter to create a digital intracardiac signal, performing a switching operation on the digital intracardiac signal received from the converter with a digital signal processor to create a switched digital intracardiac signal, and outputting the switched intracardiac signal from the system.

27. The method of claim 26 further including the step of performing a common mode noise rejection operation on the digital intracardiac signal by the digital signal processor.

28. The method of claim 26 further including the step of processing the digital intracardiac signal for gain and signal limiting and filtering the digital intracardiac signal by the digital signal processor.

29. The method of claim 26 further including the step of performing a calibration of the system to correct variations between each of a plurality of front-end amplifiers used in the amplification of the received intracardiac signal by applying digital stored calibration values to the amplified intracardiac signals received by the digital signal processor.

30. The method of claim 29 further including the step of performing a calibration of the system to correct variations between each of said plurality of front-end amplifiers used in the amplification of the received intracardiac signal by applying stored calibration values to each of the amplified intracardiac signals received by the digital signal processor.

* * * * *